(12) United States Patent
Deniega et al.

(10) Patent No.: US 6,527,957 B1
(45) Date of Patent: *Mar. 4, 2003

(54) METHODS FOR SEPARATING, COLLECTING AND STORING RED BLOOD CELLS

(75) Inventors: Jose C. Deniega, Lake Forest, CA (US); Daniel H. Duff, Irvine, CA (US); Maria D. Gudino, Mundelein, IL (US); Donald H. Buchholz, Barrington, IL (US)

(73) Assignee: Baxter International Inc., Deerfield, IL (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/287,671

(22) Filed: Apr. 7, 1999

Related U.S. Application Data

(60) Continuation-in-part of application No. 09/072,961, filed on May 5, 1998, now Pat. No. 6,080,322, and a continuation-in-part of application No. 08/819,106, filed on Mar. 18, 1997, now abandoned, which is a division of application No. 08/512,807, filed on Aug. 9, 1995, now Pat. No. 5,762,791.

(51) Int. Cl.[7] .................... B01D 61/00; A61M 1/38; A61K 35/18

(52) U.S. Cl. ............ 210/651; 210/739; 210/767; 210/782; 210/806; 435/2; 604/4.01; 604/5.01; 604/6.01; 604/6.02; 604/6.07

(58) Field of Search ............ 210/85, 86, 90, 210/109, 134, 143, 782, 787, 789, 739, 767, 806, 651, 650, 321, 67; 435/2; 494/37; 604/4, 5, 6, 65, 67, 4.01, 5.01, 6.01, 6.02, 6.07

(56) References Cited

U.S. PATENT DOCUMENTS

| | | |
|---|---|---|
| 3,916,892 A | 11/1975 | Latham, Jr. |
| 4,185,629 A | 1/1980 | Cullis et al. |
| 4,267,269 A | 5/1981 | Grode et al. |
| 4,447,191 A | 5/1984 | Bilstad et al. .......... 604/6 |
| 4,458,539 A | 7/1984 | Bilstad et al. .......... 604/6 |
| 4,464,167 A | 8/1984 | Schoendorfer et al. ...... 604/6 |
| 4,481,827 A | 11/1984 | Bilstad et al. .......... 604/6 |
| 4,498,983 A | 2/1985 | Bilstad et al. .......... 210/97 |
| 4,501,531 A | 2/1985 | Bilstad et al. .......... 604/67 |
| 4,605,503 A | 8/1986 | Bilstad et al. ...... 210/321.65 |
| 4,648,866 A | 3/1987 | Malbranoq et al. ........ 604/5 |
| 4,655,742 A | 4/1987 | Ventard .............. 604/5 |
| 4,657,529 A | 4/1987 | Prince et al. ........... 604/6 |
| 4,675,117 A | 6/1987 | Neumann et al. ........ 210/789 |
| 4,708,714 A | 11/1987 | Larsson et al. .......... 604/5 |
| 4,713,176 A | 12/1987 | Schoendorfer et al. .... 210/645 |
| 4,755,300 A | 7/1988 | Fischel et al. ...... 210/321.68 |
| 4,769,001 A | 9/1988 | Prince .................. 604/4 |

(List continued on next page.)

FOREIGN PATENT DOCUMENTS

WO       WO 97/05938       2/1997

OTHER PUBLICATIONS

Valbonesi, Et Al., "Donors Thrombocytapheresis with Last Generation Cell Separators," The International Journal of Artificial Organs, (1993), pp. 119–124, vol. 16, No. S–5.

(List continued on next page.)

Primary Examiner—John Kim
(74) Attorney, Agent, or Firm—Andrew G. Kolomayets; Bradford R. L. Price

(57) ABSTRACT

Methods are disclosed for the collection of red blood cells whereby whole blood is combined with an anticoagulant, red cells are separated from the whole blood and the separated red cells are combined with a storage solution. The red cells may be stored for an extended period of time.

9 Claims, 18 Drawing Sheets

U.S. PATENT DOCUMENTS

| | | | |
|---|---|---|---|
| 4,806,247 A | * 2/1989 | Schoendorfer et al. | 210/416.1 |
| 4,850,995 A | 7/1989 | Tie et al. | 604/6 |
| 4,851,126 A | 7/1989 | Schoendorfer | 210/651 |
| 4,879,040 A | 11/1989 | Prince et al. | 210/651 |
| 4,883,462 A | 11/1989 | Williamson et al. | 604/66 |
| 4,915,848 A | 4/1990 | Carmen et al. | 210/782 |
| 4,925,572 A | * 5/1990 | Pall | 210/767 |
| 4,935,002 A | 6/1990 | Gordon | 604/4 |
| 4,944,883 A | 7/1990 | Schoendorfer et al. | 210/782 |
| 4,961,928 A | 10/1990 | Holme et al. | 435/2 |
| 4,968,295 A | 11/1990 | Neumann | 604/6 |
| 4,985,153 A | 1/1991 | Kuroda et al. | 210/782 |
| 4,994,188 A | 2/1991 | Prince | 210/636 |
| 4,995,268 A | 2/1991 | Ash et al. | 210/87 |
| 5,034,135 A | 7/1991 | Fischel | 210/651 |
| 5,053,121 A | 10/1991 | Schoendorfer et al. | 210/90 |
| 5,069,792 A | 12/1991 | Prince et al. | 210/651 |
| 5,112,298 A | 5/1992 | Prince et al. | 604/6 |
| 5,135,667 A | 8/1992 | Schoendorfer | 210/782 |
| 5,171,456 A | 12/1992 | Hwang et al. | 210/782 |
| 5,178,603 A | 1/1993 | Prince | 604/6 |
| 5,180,504 A | 1/1993 | Johnson et al. | 210/767 |
| 5,188,588 A | 2/1993 | Schoendorfer et al. | 604/4 |
| 5,194,145 A | 3/1993 | Schoendorfer | 210/90 |
| 5,211,849 A | 5/1993 | Kitaevich et al. | 210/645 |
| 5,234,608 A | 8/1993 | Duff | 210/651 |
| 5,248,506 A | 9/1993 | Holme et al. | 435/2 |
| 5,318,512 A | 6/1994 | Neumann | 604/6 |
| 5,370,802 A | 12/1994 | Brown | 210/782 |
| 5,376,263 A | 12/1994 | Fischel | 210/651 |
| 5,387,187 A | 2/1995 | Fell et al. | 604/6 |
| 5,421,812 A | 6/1995 | Langley et al. | 604/4 |
| 5,423,738 A | 6/1995 | Robinson et al. | 604/4 |
| 5,427,695 A | 6/1995 | Brown et al. | 210/782 |
| 5,437,598 A | 8/1995 | Antwiler | 604/4 |
| 5,437,624 A | 8/1995 | Langley | 604/4 |
| 5,443,451 A | 8/1995 | Chapman et al. | 604/153 |
| 5,460,493 A | 10/1995 | Deniega et al. | 417/477.2 |
| 5,494,592 A | 2/1996 | Latham, Jr. | 210/782 |
| 5,496,265 A | 3/1996 | Langley et al. | 604/5 |
| 5,505,685 A | 4/1996 | Antwiler | 494/37 |
| 5,605,842 A | 2/1997 | Langley et al. | 436/177 |
| 5,762,791 A | 6/1998 | Deniega et al. | 210/321.67 |
| 5,783,085 A | 7/1998 | Fischel | 210/651 |

OTHER PUBLICATIONS

Valbonesi, Et Al., "Multicomponent Collection (MCS): A New Trend in Transfusion Medicine," The International Journal of Artificial Organs, (1994), pp. 65–69, vol. 17, No. 2.

Valbonesi, Et Al., Article entitled, "Platelet Pheresis Concentrates Produced in 30 Minutes Along with Plasma and Packed Red Cells: Preliminary Results," in the Journal of Clinical Apheresis, Wiley–Liss, New York, 4:152–154 (1988).

Ferrari, Et Al., Article entitled, "A New Technique for Hemodilution, Preparation of Autologous Platelet–Rich Plasma and Intraoperative Blood Salvage in Cardiac Surgery," in The International Journal of Artificial Organs, vol. 10, pp. 47–50 (1987).

Herman, Et Al., Article entitled, "Simultaneous Whole Blood Collection and Platelet Apheresis," in Journal of Clinical Apheresis, Wiley–Liss, New York, American Society For Apheresis 12th Annual Meeting, New Orleans, Mar. 20–23, 1991, Abstract 26.

Ciavarella, David, Artical entitled, "Can (Should) Apheresis Supplant Whole Blood Collection," in Transfus. Sci., Pergamon Press, Ltd., 13:201–205 (1992).

Meyer, Et Al., Article entitled, "Red Cell Collection by Apheresis Technology," in Transfusion, AABB, Bethesda, MD, 33:819–824 (1993).

Klein, Harvey G., Article entitled, "It Seemed A Pity To Throw Away the Red Cells: Selective Component Collection," in Transfusion, AABB, Bethesda, MD, vol. 33, No. 10 (Oct., 1993).

Valbonesi, Et Al., Abstract RBC Collection Along With Platelet Concentrates With The Fresenius AS104, Journal of Clinical Apheresis, Wiley–Liss, New York, 8:1; 56 (1993).

Heaton et al., "Use of Adsol® Preservation Solution for Prolonged Storage of Low Viscosity As–1 Red Blood Cells," *British Journal of Haemotology,* (57, pp. 467–478), 1984.

European Search Report dated Apr. 18, 2000.

Tomoda et al., "Acceleration of Red Cell Glycolysis by Citrate due to Intracellular pH Enhancement," *Experentia* 2915, pp. 539–540 (1972).

Tsuda et al., "Intracellular pH of Red Cells Stored in Acid Citrate Dextrose Medium," *Experentia* 28/12, pp. 1481–1482 (1972).

Tsuda et al., "Intracellular pH (pHi) of Red Cells Stored in Acid Citrate Dextrose Medium," J. Biochem., 78, pp. 469–474 (1975).

Valeri, Blood Banking and the use of Frozen Blood Products, CRC Press 1976, p. 33.

Rock et al., "Plasma Collection Using an Automated Membrane Device", Transfusion 26 (3): 269–71 (1986).

Rock et al., "Effect of Citrate Anticoagulants on Factor VIII Levels in Plasma", Transfusion 28 (3): 248–52 (1988).

Davey et al, "Preparation of White Cell–Depleted Red Cells for 42–day Storage Using an Integral In–Line Filter", Transfusion 29 (6): 496–9 (1989).

W. A. L. Heaton, et al., "Development of a Combined Storage Medium for 7–day Storage of Platelet Concentrates and 42–day Storage of Red Cell Concentrates", *British Journal of Haematology,* 1990. 75, pp. 400–407.

C. F. Hogman, "Liquid Storage of Human Erythrocytes", *Blood Separation and Plasma Fractionation,* p. 63–97, ® 1991 Wiley–Liss, Inc.

Matthes et al., "Improved Red Cell Quality After Erythroplasmapheresis with MCS–3P", J. Clinical Apheresis 9: 183–88 (1994).

Valbonesi et al., "Single–Donor Platelet Concentrates Produced Along with Packed Red Blood Cells With the Haemonetics MCS 3p: Preliminary Results", J. Clinical Aperesis: 9: 195–99 (1994).

Rugg et al., "Evaluation of ACD–A Plus RBC Additive Solutions for 42–Day Storage of Packed RBCs", *Transfusion,* vol. 36 Supplement (1996).

Dailey, "Dailey's Notes on Blood," 3d., Chapter 13, pp. 79–87, Medical Consulting Group (1996).

Haemonetics Brochure (1996).

Written Opinion from the International Preliminary Examining Authority, dated Oct. 5, 1999.

* cited by examiner

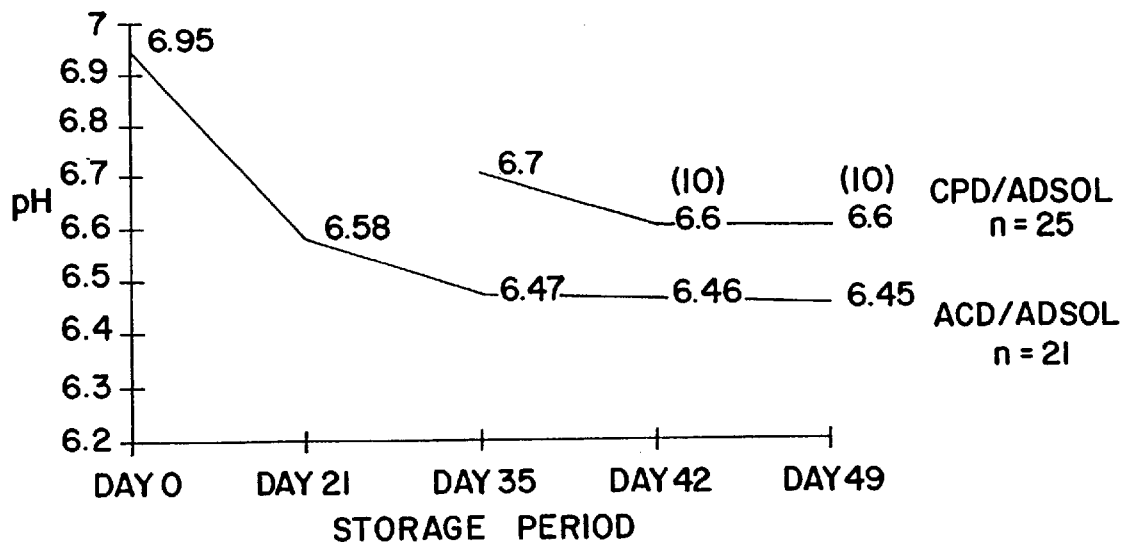
FIG.16 ACD-A/ADSOL RBC UNITS IN VITRO EVALUATION pH
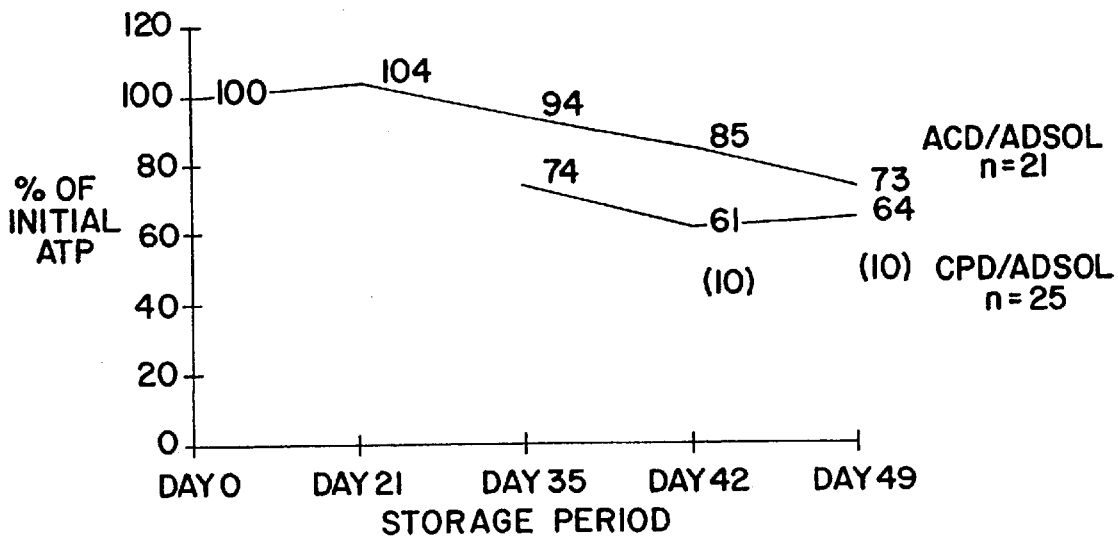
FIG.17 ACD-A/ADSOL RBC UNITS IN VITRO EVALUATION ATP

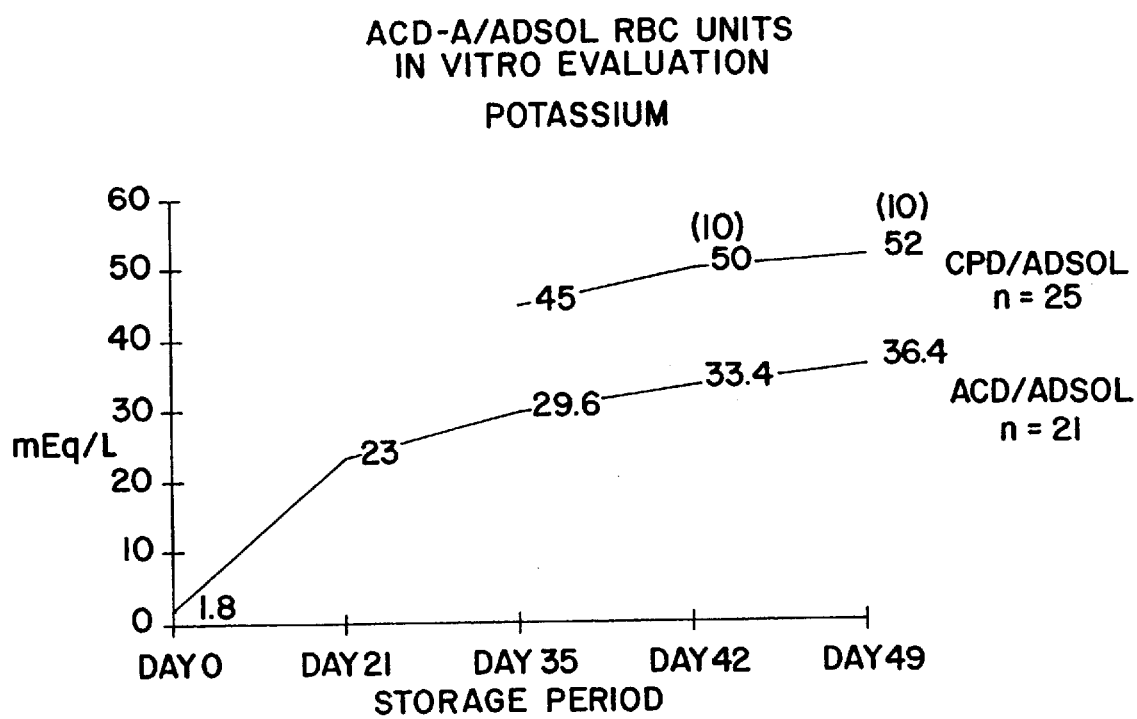
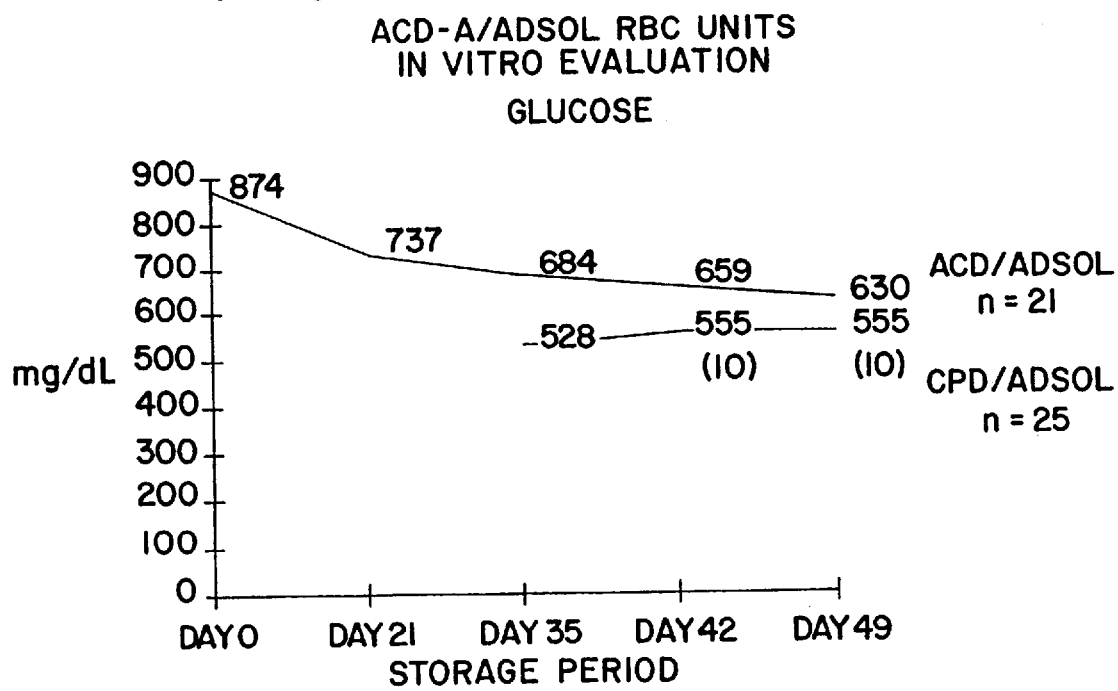

METHODS FOR SEPARATING, COLLECTING AND STORING RED BLOOD CELLS

This is a continuation-in-part of U.S. Ser. No. 08/819,106 filed Mar. 18, 1997, abandoned and a continuation-in-part of U.S. Ser. No. 09/072,961, filed May 5, 1998, U.S. Pat. No. 6,080,322, which is a divisional application of U.S. Ser. No. 08/512,807, filed Aug. 9, 1995, now U.S. Pat. No. 5,762,791.

TECHNICAL FIELD

The present invention relates generally to the separation of blood into its components such as red blood cells and plasma. More particularly, the present invention relates to the separation and collection of red blood cells whereby the red blood cells remain viable during extended storage.

BACKGROUND OF THE INVENTION

Blood may be separated into one or more of its components or fractions such as red cells, white cells, platelets and plasma, and one or more of the blood components or fractions may be collected. In typical blood collection procedures, whole blood is withdrawn from a donor or patient, anticoagulant is added to the withdrawn whole blood and one or more desired components or fractions are separated from the anticoagulated whole blood. A separated component may be administered, immediately or soon thereafter, to a patient in need of the particular component. Alternatively, the collected component may be stored for a period of time until it is required for transfusion.

Blood collection procedures and systems are often referred to as either "manual" or "automated." In "manual" blood collection procedures, whole blood is withdrawn from a donor and collected in a container that typically includes an amount of anticoagulant. After the collection, the donor is free to leave and the collected unit of whole blood is then subjected to a separation procedure, such as centrifugation.

In "automated" blood collection procedures, the donor is directly connected to a blood collection device and whole blood is withdrawn from the donor. A desired component is separated and collected while the remaining components may be returned to the donor. Automated blood collection procedures have the advantage over manual blood collection procedures in that the initial collection of whole blood and the separation of the whole blood into the desired components or fractions can be achieved in a single procedure.

Instruments used to perform automated blood collection procedures, such as those described above, typically include a reusable hardware portion and a disposable tubing portion intended for one-time use only. The hardware portion may include pumps, such as peristaltic pumps for (1) withdrawing whole blood from a donor or patient, (2) introducing anticoagulant into the whole blood (3) introducing blood into a separation device for separating blood into its components and (4) withdrawing one or more blood components from the separation device for later use or for return to the donor or patient. Either the hardware portion or the disposable tubing portion may include the separation device which, for example, can be a rotating centrifuge as described in U.S. Pat. No. 4,146,172 or a rotating membrane as described in U.S. Pat. No. 4,753,729. The disposable tubing portion typically includes, among other things, the venepuncture needle that is inserted into the donor and through which the whole blood is withdrawn, plastic tubing which transports the blood and/or blood components to and from the donor or patient and to and from the separation device. If a desired blood component is to be collected, the disposable tubing portion may also include plastic bags for collecting the desired blood component(s). Typically, the segments of the tubing are threaded over and engaged by the peristaltic pumps of the instrument. Peristaltic pumps include rotating members (rotors) driven by motors. Rotation of the pump rotors squeezes the tubing and consequently draws and pushes the blood or blood components through the tubing and through the system.

Examples of commercially available automated blood separation and collection systems are the CS-3000® Plus and the Amicus®, both sold by Baxter Healthcare Corporation of Deerfield, Ill. The CS-3000® Plus and the Amicus® are automated systems for the separation and collection of blood components and/or fractions such as platelets, plasma, and the like. Another example of a commercially available automated blood separation and collection device is the Autopheresis-C®, also sold by Baxter Healthcare Corporation. The Autopheresis C® is an automated system for the collection of plasma.

Although, commercially available devices for the automated collection of platelets, plasma, stem cells and other components are known, automated red cell collection systems have only recently been introduced. Presently, the collection of red cells is performed using the manual procedures described above.

With respect to manually collected red cells, it is known that red cells can be stored for extended periods of time (e.g. beyond 24 hours) when combined with a suitable storage media. For example, in U.S. Pat. No. 5,248,506, which is also incorporated by reference herein, manual collection of red cells from whole blood anticoagulated with a citrate-phosphate dextrose (CPD) anticoagulant and storage of the red blood cells in a red cell storage media is described. More specifically, U.S. Pat. No. 5,248,506 describes storage of red blood cells in a plasma-free storage medium that maintains the function and viability of the red cells for an extended period of time, e.g. (at least 42 days).

Factors that may affect the viability and function of stored red blood cells include ATP levels, 2,3 DPG levels, pH and the hemolysis of the red blood cells. For example, ATP (adenosine triphosphate) provides energy that is required to maintain the shape and volume of red blood cells. ATP is produced when the red blood cells metabolize glucose. Reduced ATP levels result in increased fragility of the red blood cells and, consequently, reduced viability. 2,3 diphosphoglycerate (DPG) plays a role in the red blood cell's ability to release oxygen. When 2,3 DPG levels decrease, the efficiency of oxygen release is impaired.

The pH of red blood cells must also be maintained. As the red cells break down glucose and form lactic acid, the pH of the red cell product decreases and the red blood cells undesirably become more acidic. Finally, as red blood cells are stored, they undergo hemolysis. "Hemolysis" refers to the destruction of the red blood cell membrane.

Storage solutions for storing components such as red blood cells often contain nutrients and other preservatives intended to preserve the viability of red blood cells by helping maintain acceptable ATP, 2,3-DPG and pH levels and suppressing the hemolysis of red blood cells. Although there have been several reported attempts at providing methods for preserving the viability of red blood cells during storage, further improvement in ATP levels and further reduction in hemolysis (as well as other storage parameters) is, nonetheless, still desirable.

SUMMARY OF THE INVENTION

There are several aspects to the present invention. In accordance with one aspect of the present invention, a method for collecting red blood cells is provided. The method includes providing a quantity of whole blood and combining the whole blood with a quantity of an anticoagulant. The anticoagulant includes citric acid, trisodium citrate and dextrose. The anticoagulated whole blood is separated to provide a red blood cell concentrate. The red blood cell concentrate is combined with a quantity of a solution that includes dextrose, sodium chloride, adenine and mannitol.

In accordance with another aspect of the present invention, the anticoagulated whole blood is separated to provided a red cell concentrate comprising between approximately 160–240 ml of red blood cells. The method further includes adding approximately 80–120 ml of a solution that may include, among other things, adenine, mannitol, dextrose and sodium chloride.

In accordance with another aspect of the present invention, viable red blood cells may be provided by a method which includes, among other things, establishing fluid communication between a donor and a blood separation device and removing a quantity of whole blood from a donor and combining the whole blood with a selected quantity of a phosphate-free anticoagulant. The anticoagulated whole blood is introduced into the separation device where it is separated into its components, where one of the components is concentrated red blood cells. At least a portion of at least one of the components is returned to the donor while maintaining fluid communication between the donor and the separation device. The method also includes collecting at least a portion of the separated concentrated red blood cells in a container and storing the concentrated red blood cells in a selected quantity of a solution comprising dextrose, adenine and mannitol.

In accordance with another aspect of the present invention, the method for providing viable red blood cells may include providing a separation device which includes a driven element including a separation zone to receive the anticoagulated whole blood. The method includes coupling a drive element to the driven element to cause a separation of said whole blood in the separation zone into plasma and concentrated red blood cells. The method further includes coupling an inlet pump to the driven element to convey into the separation zone whole blood from a donor selected from the population of blood donors, wherein the whole blood of the selected blood donor having a known beginning hematocrit value that varies within the population of blood donors, according to the morphology of the selected blood donor. In accordance with a further aspect of the present invention, the method includes commanding the inlet pump element and the drive element as a function of the known beginning hematocrit value to obtain concentrated red blood cells having an end hematocrit value that remains substantially constant for the population of blood donors despite variances in the known beginning hematocrit value according to the morphology of the selected blood donors.

BRIEF DESCRIPTION OF THE DRAWINGS

FIG. 16 is a graph comparing the pH levels of stored red blood cell compositions prepared in accordance with the present invention and red blood cell compositions prepared by a different method;

FIG. 17 is a graph comparing ATP levels of stored red blood cell compositions prepared in accordance with the present invention and red blood cell compositions prepared by a different method;

FIG. 18 is a graph comparing potassium levels of stored red blood cell compositions prepared in accordance with the present invention and red blood cell compositions prepared by a different method;

FIG. 19 is a graph comparing glucose levels of stored red blood cell compositions prepared in accordance with the present invention and red blood cell compositions prepared by a different method;

DETAILED DESCRIPTION

As set forth above, in one aspect, the present invention is directed to a method for providing viable red blood cells. Also, as set forth above, the method generally includes collecting whole blood in a phosphate-free anticoagulant including citric acid, trisodium citrate and dextrose, separating the whole blood into its components including concentrated red blood cells and storing the concentrated red blood cells in a solution including dextrose, mannitol and adenine.

It will be understood that the method of the present invention may be practiced as part of a manual, but more preferably, an automated blood separation and collection technique as described above. Automated systems that may be used to practice the method of the present invention may include the above described CS-3000® Plus and Amicus® cell separators (which systems include centrifugal separators) sold by Baxter Healthcare Corporation. In addition to the centrifugal separators described above, the present invention may also be practiced using a separation device that includes a spinning rotor and membrane for separating blood components, such as the rotor and membrane used in the above-identified Autopheresis® C, also sold by Baxter Healthcare Corporation.

The present invention will be described in the context of one specific system which is set forth in more detail below. The exemplary system uses a separation device that employs a spinning rotor and a membrane to separate concentrated red blood cells. It should be understood, however, that the system described below is but one example of a system useful in practicing the present invention and that the method of the present invention is not limited to this system.

Figure 1:
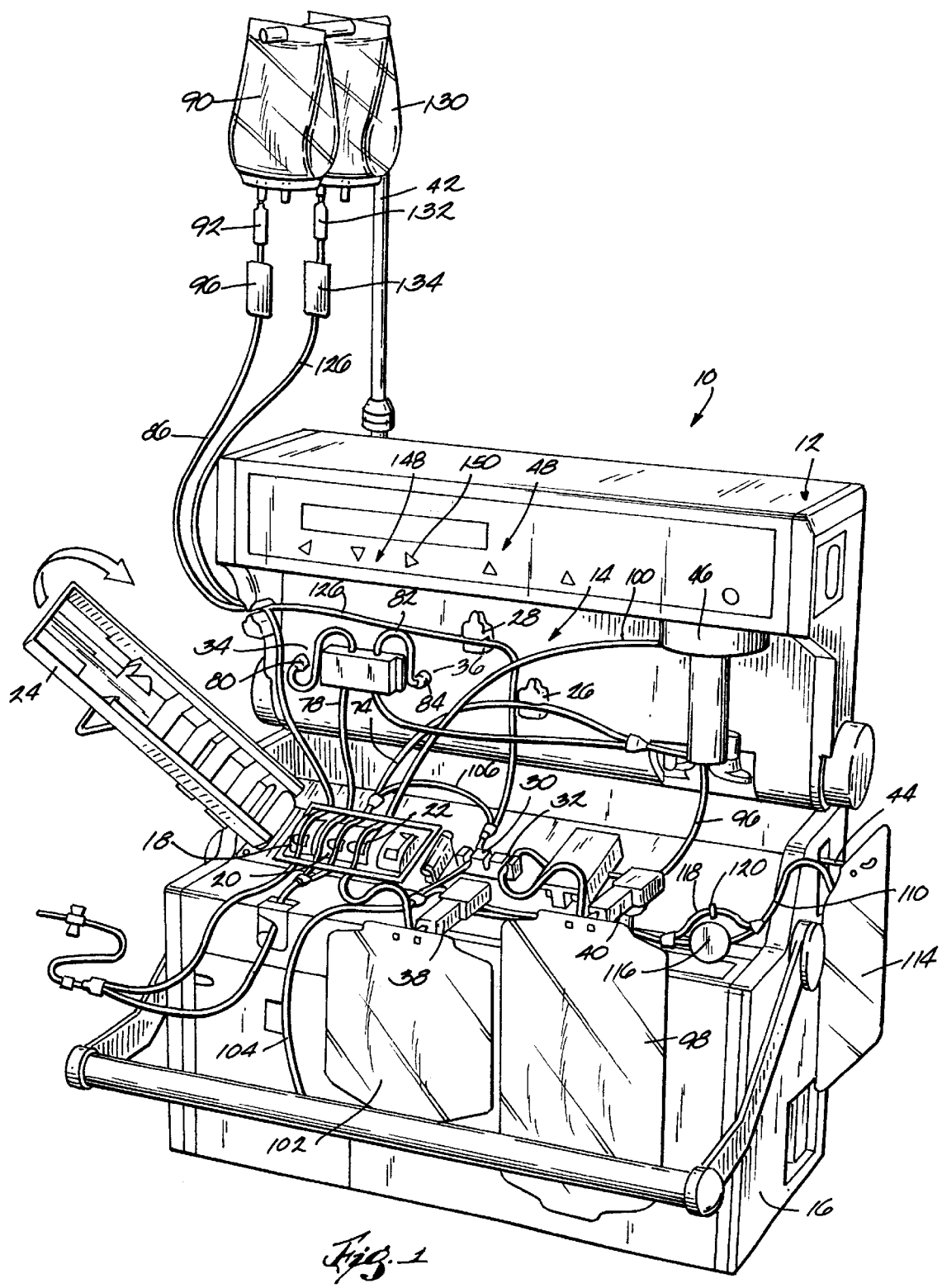
FIG. 1 is a perspective view of a blood collection system of the present invention, comprising a disposable blood processing set including a rotating microporous membrane assembly mounted on a durable blood processing device.

FIG. 1 shows a blood collection system 10 that serves to collect concentrated red blood cells from donors in uniformly high hematocrits comparable to those achieved by manual collection procedures, while at the same time collecting plasma in uniformly increased volume amounts comparable to those achieved by at least manual plasmapheresis procedures. The system 10 achieves these dual objectives in an automated fashion, by processing a donor's whole blood extra-corporeally over a relatively short period of time such as 20–40 minutes (and typically less than 30 minutes), using a single phlebotomy needle in successive blood draw and blood return cycles. The details of these cycles will be described later.

Figure 2:
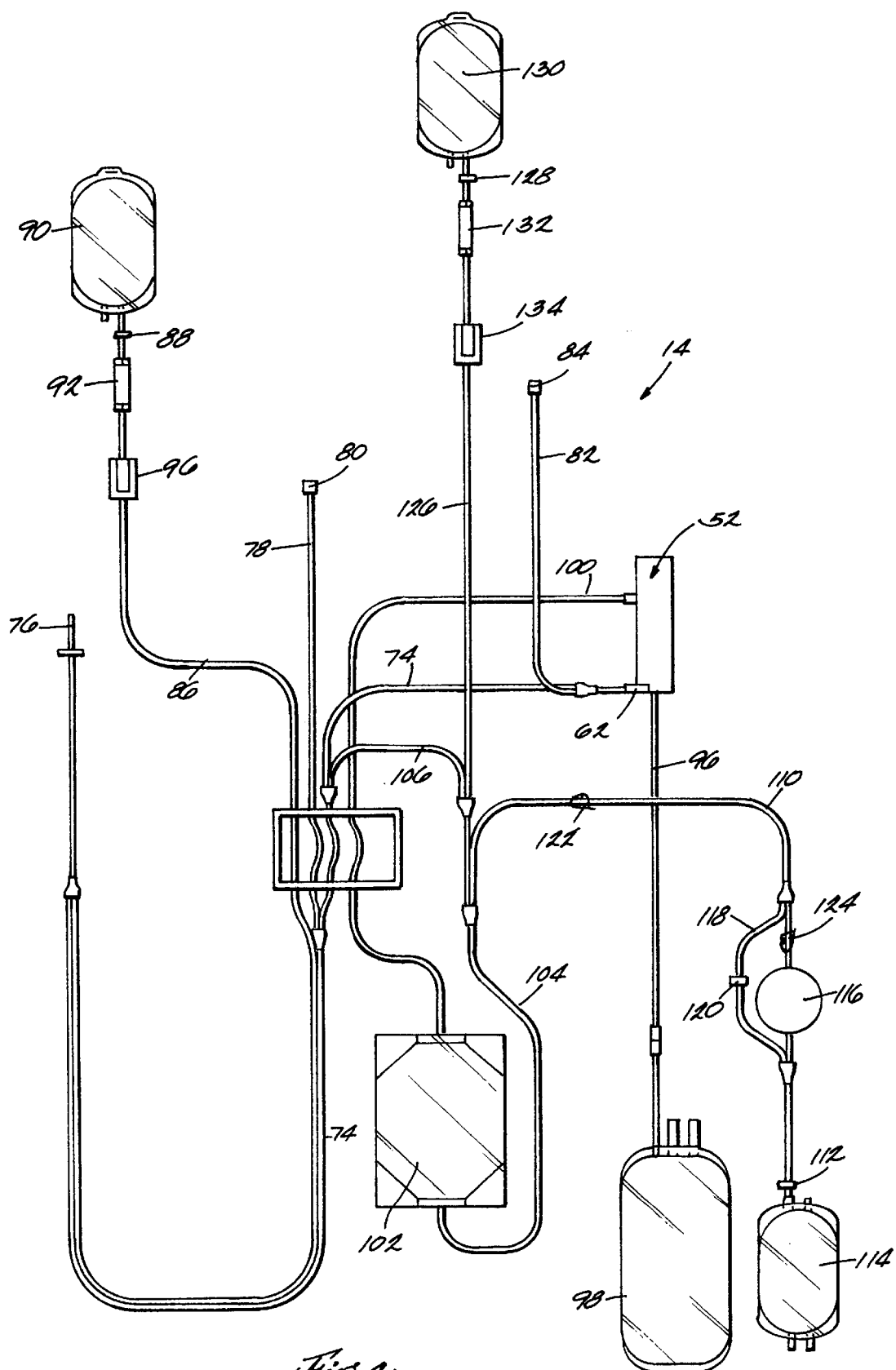
FIG. 2 is a schematic view of the disposable blood processing set associated with the blood collection system shown in FIG. 1.

As FIG. 1 shows, the system 10 includes a blood processing device 12, which constitutes a durable hardware element. The system 10 also includes a blood processing set 14 (see FIG. 2 as well), which constitutes a single use, disposable element. At the outset of a blood processing procedure, the operator mounts the set 14 (as FIG. 2 shows) in a prescribed fashion upon the device 12 (as FIG. 1 shows). At the end of the blood processing procedure, the operator removes the set 14 from the device and discards it, except for containers in which blood components are collected for storage or further processing after the donor has departed.

A. The Blood Processing Device

Referring to FIG. 1, the blood processing device 12 includes a cabinet 16 carrying various electrically operated elements. These elements include first, second, and third peristaltic pumps, respectively 18, 20, and 22. A pump cover 24, common to the pumps 18/20/22, pivots to open and close access to the pumps 18/20/22. FIG. 1 shows the pump cover 24 to be open, and the closing of the pump cover 24 is indicated by an arrow in FIG. 1. All pumps 18/20/22 are capable of operation at variable speeds under the command of an on board microprocessor-based controller 48, as will be described later. The controller 48 receives input from the operator regarding desired operating objectives and issues commands to the operative elements of the device 12 to achieve them.

The operative elements also include first, second, third, and fourth tubing clamps, respectively 26, 28, 30, and 32. In the illustrated and preferred embodiment, the clamps 26/28/30/32 are of a conventional, electrically actuated variety under the command of the controller 48.

The operative elements further include first and second pressure sensors 34 and 36; first and second weight scales 38 and 40; and container supports 42 and 44. The operative elements also include a motor-driven driver 46. Operation of all these elements, except the passive supports 42 and 44, is commanded by the controller 48.

Addition details of the structure these operative elements are not essential to the understanding of the invention. However, such additional details are disclosed in copending patent application Ser. No. 08/153,615, entitled "Peristaltic Pumping Assembly," filed Nov. 17, 1993 and are incorporated herein by reference.

B. The Blood Processing Set

Figure 3:
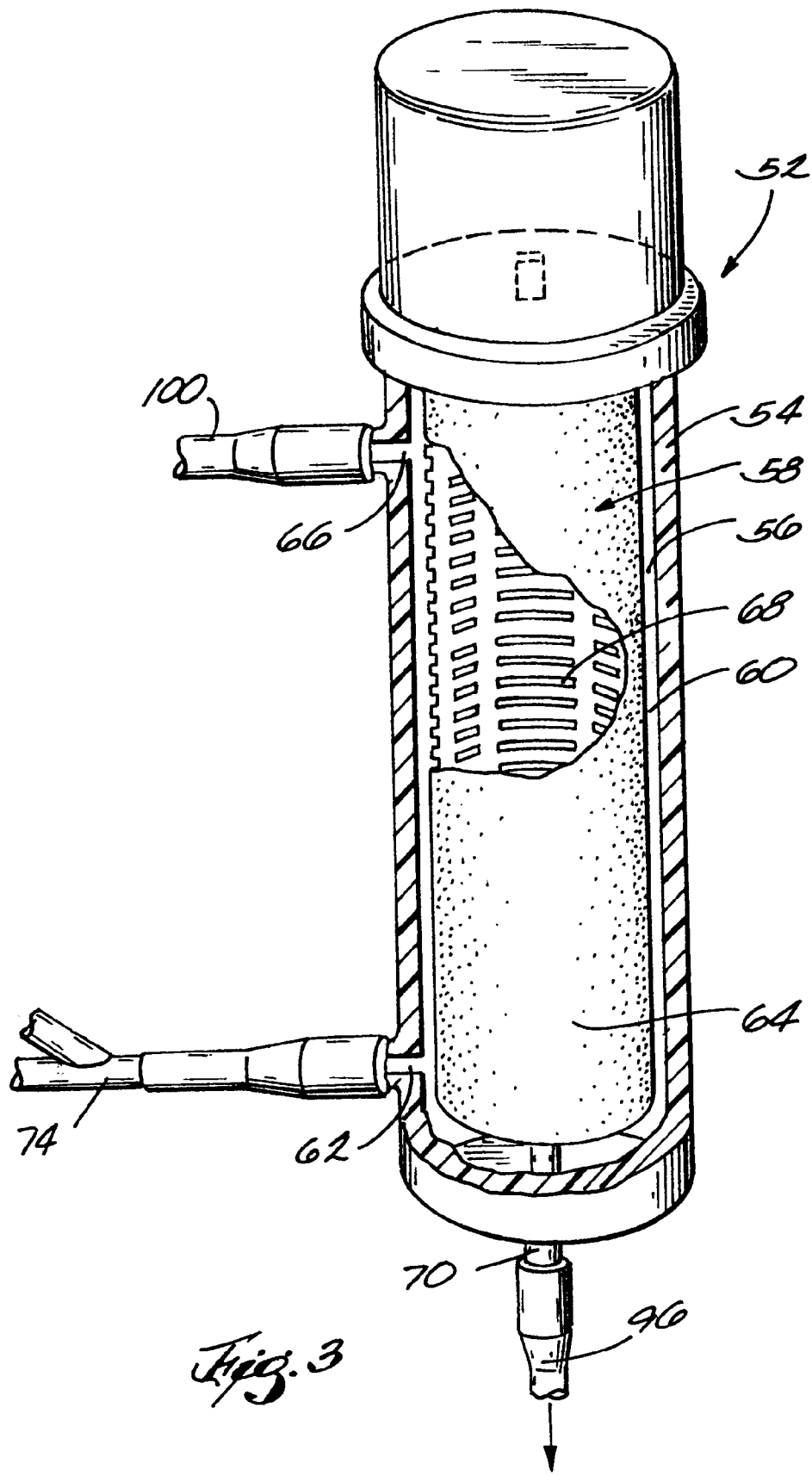
FIG. 3 is a perspective view, partially broken away and in section, of the rotating microporous membrane assembly that forms a part of the disposable blood processing set shown in FIG. 2.

Referring now principally to FIGS. 2 and 3, the blood processing set 14 includes a membrane filtration device 52 that separates whole blood into its cellular and non-cellular components. The device 52 is described and claimed in Fischel U.S. Pat. No. 5,034,135, previously referred to, which is incorporated herein by reference.

The device 52 (see FIG. 3) includes a housing 54 having an interior wall 56. The housing 54 carries an interior rotor or spinner 58. A gap 60 extends between the exterior of the rotor 58 and the housing's interior wall 56. The gap 60 constitutes a zone where blood separation occurs.

In the illustrated embodiment, the gap 60 has a width of about 0.020 inch and a length of about 3.0 inches. An inlet 62 leads into the gap 60 at the bottom of the separation zone.

The rotor 58 carries a microporous membrane 64. The pore size of the membrane 64 is in the range of about 0.4 $\mu$m to 0.8 $\mu$m. The pores of the membrane 64 allow passage of the noncellular plasma constituent of whole blood.

The separated cellular components, which remain in the gap 60, exit the separation zone through a first outlet 66. A series of channels 68 on the rotor 58 behind the membrane 64 carry the noncellular plasma component to a second outlet 70.

Bearings (not shown) carry the rotor 58 for rotation within the housing 54. In use, the housing 54 is mounted on the cabinet 16 (see FIG. 1), where the rotor 58 is magnetically coupled to the driver 46. The driver 46 rotates the rotor 58 at a selected surface velocity. When rotated, the membrane-carrying rotor 58 creates movement of the whole blood in the gap 60. This movement (which takes the form of vortices technically known as Taylor Vortices) induces transport of the cellular components away from the membrane 64 while the noncellular plasma component is transported to the membrane 64 for filtration through the membrane 64. Enhanced membrane separation of plasma from red blood cells (and platelets and leukocytes) occurs.

It should be appreciated that, in an alternative embodiment, the interior wall 56 of the housing 54 could carry the membrane 64. Rotation of the rotor 58 (which, in this alterative embodiment, is free of a membrane) will cause the same vortices to develop and lead to the same enhanced separation results.

Anticoagulated whole blood is introduced into separation device 52 at whole blood inlet port 62. Once inside the separator, which in FIGS. 1 and 2 includes a rotating spinning membrane as generally described in U.S. Pat. Nos. 4,753,729, 5,034,135 and 5,194,145, all incorporated by reference herein, the anticoagulated whole blood is separated into packed or concentrated red cells and plasma. The rotor may be rotated at a speed of between approximately 3600–3900 with a preferred speed of approximately 3800 rpm. During the procedure, which typically takes between 20–40 minutes, anywhere between 1000–2000 ml of whole blood may be processed. Typically, however, the volume of whole blood processed is between 1200–1400 ml.

Referring back to FIG. 2, the set 14 includes an array of flexible medical grade plastic tubing that conveys fluid into and out of the separation device 52. A first tube 74 carrying a phlebotomy needle 76 communicates with the whole blood inlet 62 of the separation device 52. In use (see FIG. 1), the first tube 74 is strung on the cabinet 16 in operative association with the second peristaltic pump 20. The pump 20 conveys whole blood through the first tube 74 from a donor into the gap 60 for separation. Also in use, the portion of the tube 74 downstream of the pump 20 makes operative contact with the clamp 26. Under the control of the controller 48, the clamp 26 thereby serves to open and close blood flow through the first tube 74.

A first auxiliary branch 78 coupled to the first tube 74 carries a pressure transducer 80 for sensing whole blood pressure downstream of the pump 20. In use (see FIG. 1), the transducer 80 is mounted in operative association with the pressure sensor 34 on the cabinet 16. The sensor 34 monitors the donor's vein pressure, generating an output P1, which will be described in greater detail later.

A second auxiliary branch 82 coupled to the first tube 74 near the inlet 62 carries a pressure transducer 84. In use (see FIG. 1), the transducer 84 is mounted in operative association with the pressure sensor 36 on the cabinet. The sensor 36 thereby monitors whole blood pressure entering the separation gap 60, which closely corresponds with the pressure across the membrane 64, called transmembrane pressure or TMP. The output of the sensor 36 is referred to as P2, which will be described in greater detail later.

A second tube 86 communicates with the first tube 74 near the phlebotomy needle. The second tube 86 carries a conventional spike coupler 88 for connection to a container 90 holding a conventional anticoagulant, like ACD. The second tube 86 also includes an in line drip chamber 92 and sterility filter 96.

In use, the container 90 is hung on the support 42 above the cabinet 16. Also in use (see FIG. 1), the second tube 86 is strung in operative association with the first pump 18. The first pump 18 thereby serves to convey anticoagulant into the whole blood conveyed by the second pump 20. The controller 48 drives the first pump 18 at a prescribed rate relative to the second pump 20 to meter anticoagulant into the whole blood in a set ratio, which may be between approximately 1 volume part anticoagulant to 8 to 14 volume parts of whole blood and is typically about 1 volume part of anticoagulant to 8 to 10 or 12 volume parts of whole blood. In one embodiment, a preferred ratio may be 1 volume part of anticoagulant to 12 volume part whole blood (i.e., 8% ACD whole blood).

A third tube 97 communicates with the second outlet 70 of the separation device 52 to convey plasma from the separation gap 60 to a connected container 98. In the illustrated and preferred embodiment, the container 98 is integrally connected to the third tube 96. In use (see FIG. 1), the third tube 97 is mounted on the cabinet 16 to make operative contact with the clamp 32. The clamp 32 thereby serves to open and close plasma flow through the third tube 97 into the container 98, as commanded by the controller 48. Also in use, the container 98 is hung in association with the weight scale 40. Through the weight scale 40, the controller 48 monitors the volume of plasma collecting in the container 98.

A fourth tube 100 communicates with the first outlet 66 of the separation device 52 to convey red blood cells (with associated platelets and leukocytes) from the separation gap 60 to a connected container 102. In the illustrated and preferred embodiment, the container 102 is integrally connected to the fourth tube 100, which enters at the top of the container 102 (see FIG. 2).

In use (see FIG. 1), the fourth tube 100 is strung in operative association with the third pump 22. The pump 22 thereby serves to convey red blood cells (with associated platelets and leukocytes) from the separation gap 60 to the container 102, as commanded by the controller 48. Also in use, the container 102 is hung in association with the weight scale 38. Through the weight scale 38, the controller 48 monitors the volume of red blood cells collecting in the container 102.

A fifth tube 104 communicates with the container 102. In the illustrated and preferred embodiment, the fifth tube 104 is integrally connected at the bottom of the container 102 (see FIG. 2).

In use (see FIG. 1), the fifth tube 104 is mounted on the cabinet 16 to make operative contact with the clamp 30. The clamp 30 thereby serves to open and close red blood cell flow through the fifth tube 104 from the container 102, as commanded by the controller 48. An auxiliary branch 106 couples the first tube 74 in fluid flow communication with the fifth tube 104 upstream of the clamp 30.

The pump 20 is capable of operation in reverse directions under the direction of the controller 48. The pump 20 thereby serves, when operated in a clockwise direction with the clamp 26 opened and the clamp 30 closed, to draw whole blood from the donor in a first direction through the tube 74 into the separation device 52. When operated in a counter-clockwise direction with the clamp 26 closed and the clamp 30 opened, the pump 20 also serves to draw red blood cells from the container 102 in a reverse direction through tube 74 for return to the donor.

A sixth tube 110 also communicates with the fifth tube 104. The sixth tube 110 may be integrally connected to a container 114 holding a storage solution for the red blood cells. One such solution is disclosed in Grode et al U.S. Pat. No. 4,267,269, which solution is commercially available and is sold under the name ADSOL® by Baxter Healthcare Corporation. Another such solution is conventionally called "SAG-M" solution. In use (see FIG. 1), the container 114 is hung on the support 44 at the side of the cabinet 16.

The sixth tube 110 also includes an in line filter 116 containing a conventional fibrous filtration medium suited for the removal of leukocytes from red blood cells. The filtration medium can include cotton wool, cellulose acetate or another synthetic fiber like polyester. The filter 116 can be commercially procured, for example, from the Pall Corporation (PALL™ WBF1) or Asahi Medical Company (SEPACELL™ RS2000).

A bypass tube 118 joins the sixth tube 110 upstream and downstream of the filter 116. The bypass tube 118 includes an in line, one-way valve 120 for allowing fluid flow in a direction away from, but not toward, the container 114. The sixth tube 110 also includes a conventional manual roller clamp 122 near the junction of the sixth tube 110. Another conventional manual roller clamp 124 is also present in the sixth tube 110 between the upstream end of the filter 116 and the upstream junction between the sixth tube 110 and bypass tube 118.

A seventh tube 126 communicates with the auxiliary branch 106. The seventh tube 126 carries a conventional spike coupler 128 for connection to a container 130 holding a sterile fluid, like saline. The seventh tube 126 also includes an in line drip chamber 132 and sterility filter 134. In use (see FIG. 1), the container 130 is hung on the support 42 above the cabinet 16, next to the anticoagulant container 90. The seventh tube 126 is also mounted on the cabinet 16 to make operative contact with the clamp 28. The clamp 28 thereby serves to open and close sterile fluid flow from the container 130, as commanded by the controller 48.

The sterile fluid is used to initially prime the disposable set 14 before use. And, as will be described in greater detail later, the sterile fluid can also be used as a replacement fluid conveyed to the donor at certain stages of blood processing.

Finally, as seen, for example, in FIGS. 1 and 2 a tubing organizer 131 is placed over and peristaltic pumps 18/20/22. Placement of the processing set 14 with tubing organizer 131 onto the device 12 is described in greater detail in U.S. Pat. No. 5,460,493 and U.S. patent application Ser. No. 08/779,094 entitled "Disposable Tubing Set and Organizer Frame for Holding Flexible Tubing," filed Jan. 6, 1997, now U.S. Pat. No. 5,870,805, in the name of J. Kandler, M. Moubayed and M. Vandlik and assigned to the assignee of the present application. U.S. Pat. No. 5,460,493 and U.S. Ser. No. 08/779,094, now U.S. Pat. No. 5,870,805, are incorporated by reference herein.

C. The Controller

Figure 11:
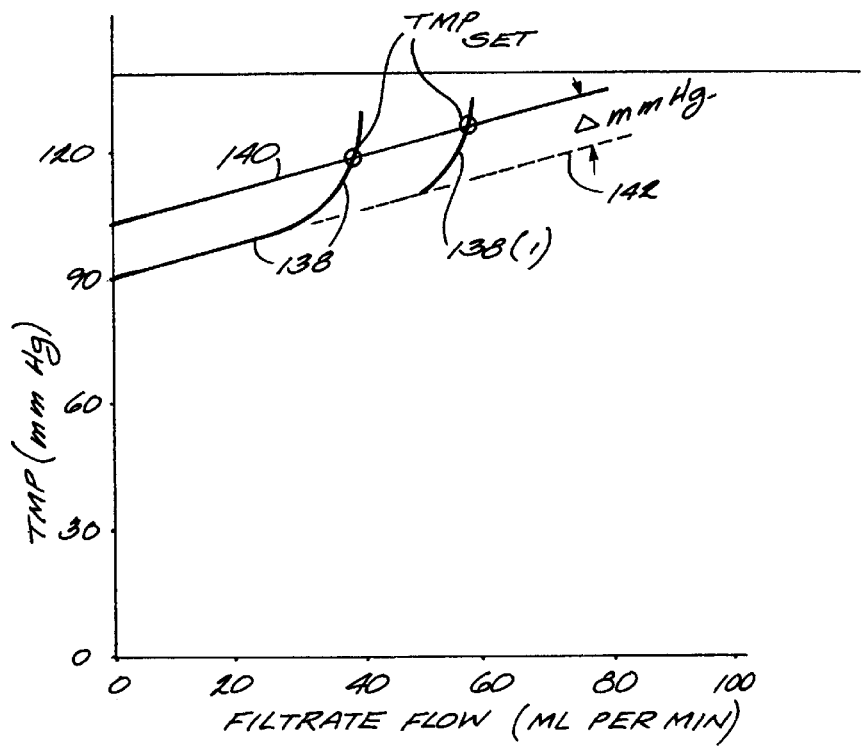
FIG. 11 is a graph showing an enhanced fluid characteristic curve and its intersection with a control curve to establish an elevated set point for transmembrane pressure that optimizes plasma separation efficiency, particularly for lower donor hematocrits.

The flow of plasma filtrate through the outlet 70 will increase linearly as TMP increases, until the TMP forces red blood cells into the membrane 64, blocking it. At this point the TMP rises steeply in a non-linear manner. This relationship between TMP and plasma flow rate defines a fluid characteristic curve for each combination of whole blood flow rate (which is the rate at which the whole blood inlet pump 20 is operated and will be referred to as $RATE_{WB}$), speed of rotation of the rotor 58 (which the controller 48 commands through the driver 46 and will be referred to as ROTOR), and whole blood hematocrit of the donor (which will be referred to as $HCT_{WB}$). FIG. 11 shows a representative fluid characteristic curve 138 for one such combination.

Figure 12:
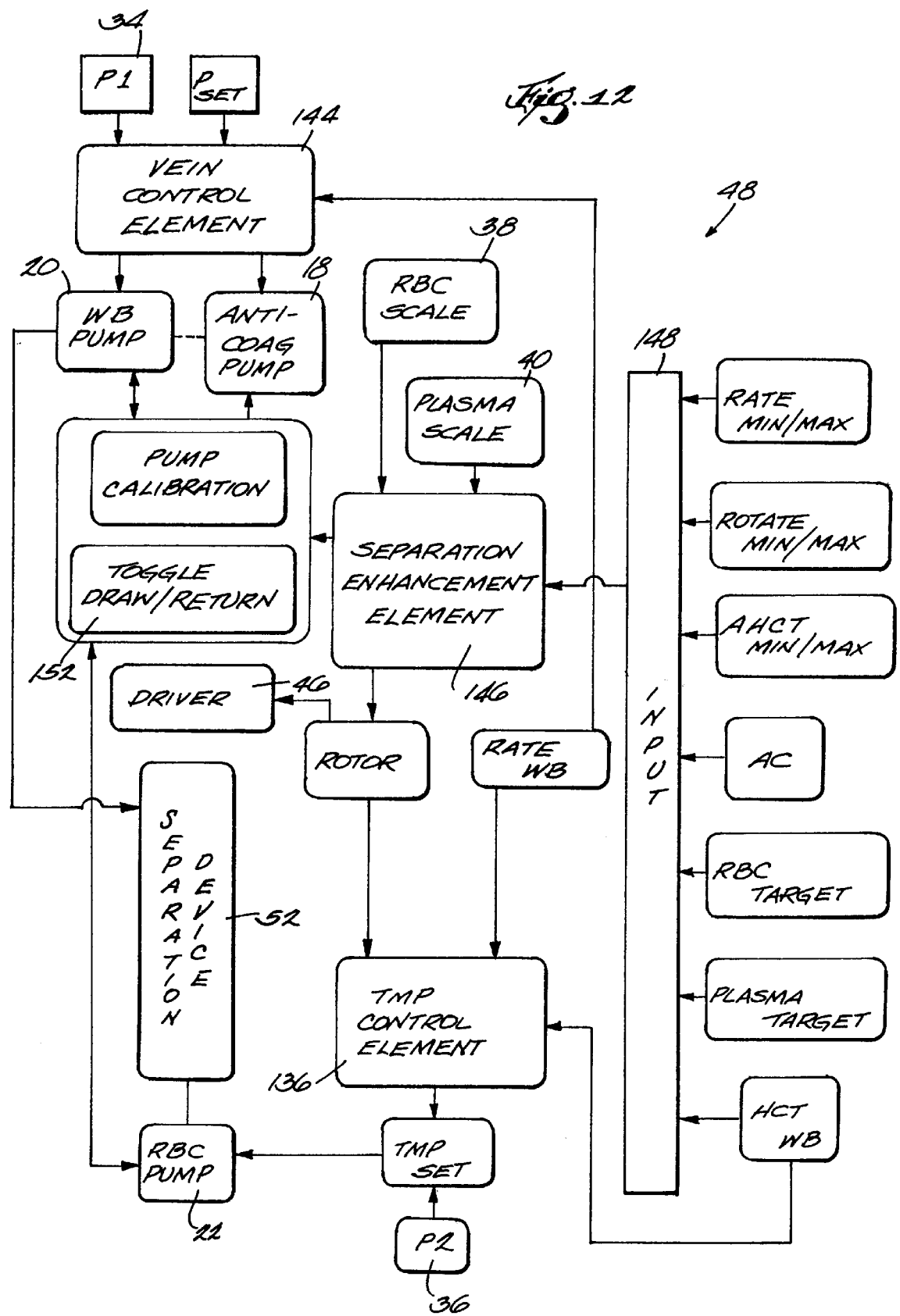
FIG. 12 is a schematic view of the elements of the controller associated with the system shown in FIG. 1, including a separation enhancement element that augments the operation of the TMP control element and vein control element of the controller to separate red blood cells of a uniformly high hematocrit, regardless of donor hematocrit.

As FIG. 12 shows, the controller 48 includes a TMP control element 136. The element 136 monitors pressure P2 sensed by sensor 36 at the whole blood inlet 62 of the separation device 52. As before explained, pressure P2 essentially represents the TMP of the separation device 52. The control element 136 compares the sensed TMP to a set TMP (designated $TMP_{SET}$) and varies the pumping rate of the red blood cell pump 22 to stabilize sensed TMP (i.e., P2) at $TMP_{SET}$.

As FIG. 11 shows, $TMP_{SET}$ lies at the intersection of the fluid characteristic curve 138 and a control curve 140. The TMP control element 136 derives the control curve 140 at the outset of every procedure. The control element 136 initially measures P2 at one low filtrate rate and fits a straight line curve having a given slope to the initial sensed point. The slope of the curve, expressed in terms of change of TMP ($\Delta TMP$) over the change in the flow rate of plasma ($\Delta RATE_P$), is a function of the type of microporous membrane 64 used. For example, when the microporous membrane 64 comprises a nylon material, the slope is 26. When the microporous membrane comprises a polycarbonate material, the slope is 13.

In this way, the controller 136 forms a linear prediction curve 142 (shown in phantom lines in FIG. 11). As FIG. 11 shows, the linear portion of the fluid characteristic curve 138 typically follows the slope of the linear prediction curve 142. The TMP control element 136 translates the linear prediction curve 142 upward by a prescribed, empirically determined amount, designated $\Delta mm$ Hg in FIG. 11. In the illustrated embodiment, the positive offset $\Delta mmHg$ between the linear prediction curve 142 and the control curve 140 is about 24 mm Hg.

Further details of the derivation of the fluid characteristic curve 138 and the control curve 140 are not essential to the invention. These details are set forth in U.S. Pat. No. 4,879,040, which is incorporated herein by reference.

As FIG. 12 also shows, the controller 48 further includes a vein control element 144. The element 144 monitors pressure P1 sensed by sensor 34 downstream of the whole blood pump 20 (see FIG. 4). Pressure P1 essential represents the vein pressure of the donor, which is a negative pressure. A decrease in vein pressure P1 below an empirically determined amount ($P1_{SET}$) indicates the collapse of the phlebotomy vein. The control element 144 continuously compares the sensed P1 with $P1_{SET}$ and varies the pumping rate of the whole blood inlet pump 20 ($RATE_{WB}$) to maximize the numerical value of P1 without exceeding the numerical value of $P1_{SET}$.

Further details of the vein control element 144 are not essential to the invention. These details are described in U.S. Pat. No. 4,657,529, which is incorporated herein by reference.

The TMP control element 136 and the vein control element 144 operating as just described will provide plasma separation efficiency (EFF) that varies according to $HCT_{WB}$ as set forth in the following Table 1:

TABLE 1

| $HCT_{WB}$ | EFF | $HCT_{RBC}$ |
|---|---|---|
| 38.5% | 63% | 63% |
| 45% | 56% | 65% |
| 52.5% | 55% | 71% | where:

$$EFF (\%) = \frac{RATE_P}{RATE_{WB} \times (1 - HCT_{WB})} \quad (1)$$

where:
RATE$_P$ is the flow rate of plasma through the outlet 170.
RATE$_{WB}$ is the flow rate of whole blood through the inlet 62.

Table 1 shows that EFF increases as HCT$_{WB}$ decreases. Still, as Table 1 shows, the increase in EFF is not enough at lower HCT$_{WB}$ values to maintain a concentrated red blood cell hematocrit (HCT$_{RBC}$) at or near 70%.

According to the invention, the controller 48 augments the operation of the TMP control element 136 and the vein control element 144 to separate red blood cells suitable for collection and long term storage at high concentrations (i.e., about 70% hematocrit) for all values of HCT$_{WB}$ typically encountered in normal healthy blood donors (i.e., from about 38% hematocrit to about 56% hematocrit and more). At the same time, the controller 48 maintains high plasma separation efficiencies to yield from the same red blood cell donor about 450 ml to 500 ml of plasma suitable for collection, fractionation, or long term storage.

The inventors have discovered that increasing the rotational speed (ROTOR) of the rotor 58 during separation has the effect of extending the linear portion of the fluid characteristic curve without trauma to red blood cells, creating an enhanced fluid characteristic curve 138(1), shown in FIG. 11. As FIG. 11 shows, the new fluid characteristic curve 138(1) intersects the control curve 140 at higher point, resulting in a higher TMP$_{SET}$. Operating at a higher TMP$_{SET}$ results in a higher RATE$_P$ and, therefore, a higher EFF.

The inventors have also discovered that there is a critical interrelationship among HCT$_{WB}$, ROTOR (expressed in revolutions per minute or RPM), and RATE$_{WB}$ (expressed in ml/min) that, in combination with TMP control at TMP$_{SET}$, optimizes EFF to achieve consistent, high HCT$_{RBC}$ for all normal donor HCT$_{WB}$. This interrelationship in effect defines a family of enhanced fluid characteristic curves 138(1) for combinations of HCT$_{WB}$, ROTOR, and RATE$_{WB}$. The intersections of the enhanced fluid characteristic curves 138(1) with the control curve 140 define a family of higher TMP$_{SET}$ points. The higher TMP$_{SET}$ points produce, over the range of normal HCT$_{WB}$, both a consistent, uniform high yield of plasma (about 400 ml to 450 ml) and a likewise consistent, uniform high yield of red blood cells (about 250–275 ml) at a relatively high concentration (HCT$_{RBC}$ of about 70%).

Figure 13:
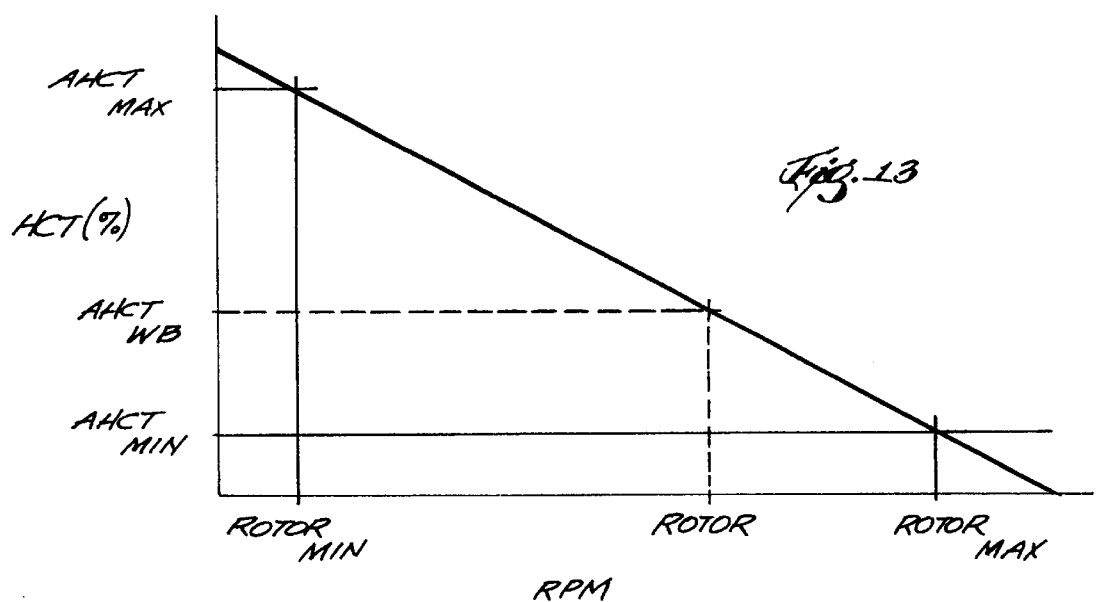
FIG. 13 is a graph showing the relationship between donor hematocrit and the speed of rotation of a rotary membrane separation device that the separation enhancement element of the controller implements to produce red blood cells of a uniformly high hematocrit, regardless of donor hematocrit.

FIG. 13 shows in graphical form the just described relationship discovered between HCT$_{WB}$ and ROTOR for a rotating membrane separation device 52 of the type described above. FIG. 13 demonstrates the general principle, that, as HCT$_{WB}$ decreases, ROTOR must be increased to optimize EFF sufficient to obtain a consistent, uniform high HCT$_{RBC}$. The relationship expressed in the graph in FIG. 13 can be expressed mathematically as follows:

$$\frac{AHCT_{MAX} - AHCT_{WB}}{ROTOR - ROTOR_{MIN}} = \frac{AHCT_{MAX} - AHCT_{MIN}}{ROTOR_{MAX} - ROTOR_{MIN}} \quad (2)$$

where:
AHCT$_{MAX}$ is the maximum anticoagulated hematocrit of whole blood that will be processed. This value is derived as follows:

$$AHCT_{MAX} = HCT_{MAX} \times (1-AC) \quad (3)$$

where:
HCT$_{MAX}$ is the set maximum donor whole blood hematocrit that will be processed. This value is set by the manufacturer taking into account prevailing governmental regulations and clinical experience with the particular separation device 52. For the separation device 52 described above, a nominal value for HCT$_{MAX}$ of about 57 can be used.
AC is the selected anticoagulant ratio. For example, for an anticoagulant ratio of 8%, AC=0.08.
AHCT$_{MIN}$ is the minimum anticoagulated hematocrit of whole blood that will be processed. This value is derived as follows:

$$AHCT_{MAX} = HCT_{MIN} \times (1-AC) \quad (4)$$

where:
HCT$_{MIN}$ is the set minimum donor whole blood hematocrit that will be processed. This value is also set by the operator taking into account prevailing governmental regulations and clinical experience with the particular separation device 52. For the separation device 52 described above, a nominal value for HCT$_{MIN}$ of about 38 can be used.
AHCT$_{WB}$ is the anticoagulated hematocrit of the donor's whole blood entering the separation device 52, derived as follows:

$$AHCT_{WB} = HCT_{WB} \times (1-AC) \quad (5)$$

ROTOR$_{MAX}$ and ROTOR$_{MIN}$ are, respectively, the maximum and minimum rotational speeds set for the rotor 58 for the prescribed range of hematocrits between AHCT$_{MIN}$ and AHCT$_{MAX}$. These speeds are preestablished by the manufacturer, taking into account operational constraints of the driver 46, the separation device 52, and clinical or experimental experience with the separation device 52. ROTOR$_{MAX}$ takes into account clinical or experimental data regarding the onset of clinically significant trauma to cellular components when exposed to the high shear conditions within the rotating membrane separation device 52, given the prescribed range of hematocrits between AHCT$_{MIN}$ and AHCT$_{MAX}$. ROTOR$_{MIN}$ takes into account clinical or experimental data regarding the onset of Taylor Vortex conditions within the gap 60 of the device 52 sufficient to create movement of cellular components away from the rotating membrane 64 while plasma is carried toward the rotating membrane 64 for collection, also given the prescribed range of hematocrits between AHCT$_{MIN}$ and AHCT$_{MAX}$. For the separation device 52 described above, and given the range of minimum and maximum hematocrits of 38% to 56%, nominal values of ROTOR$_{MAX}$=4000 RPM and ROTOR$_{MIN}$3600 RPM can be used.

Solving Equation (2) for ROTOR yields the following expression:

$$ROTOR = ROTOR_{MAX} - \left[ \frac{ROTOR_{MAX} - ROTOR_{MIN}}{AHCT_{MAX} - AHCT_{MIN}} \times (AHCT_{WB} - AHCT_{MIN}) \right] \quad (6)$$

Figure 14:
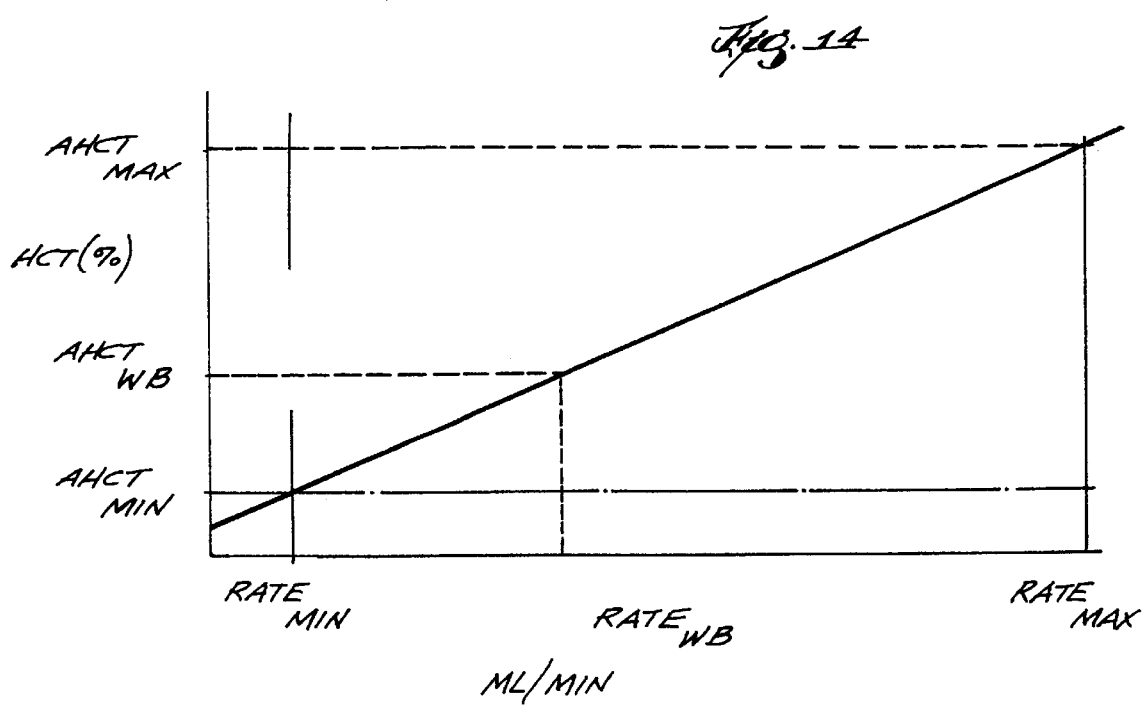
FIG. 14 is a graph showing the relationship between donor hematocrit and the flow rate of whole blood into a rotary membrane separation device that the separation enhancement element of the controller implements to produce red blood cells of a uniformly high hematocrit, regardless of donor hematocrit.
Figure 20:
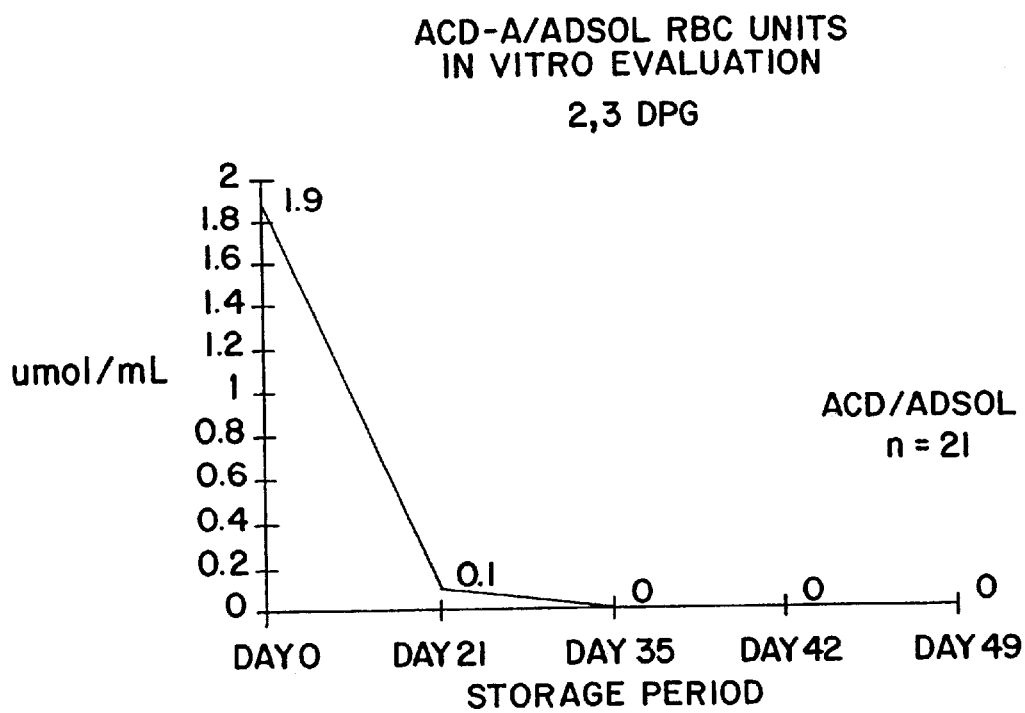
FIG. 20 is a graph showing the level of 2,3 DPG of stored red blood cell compositions prepared in accordance with the present invention.
Figure 21:
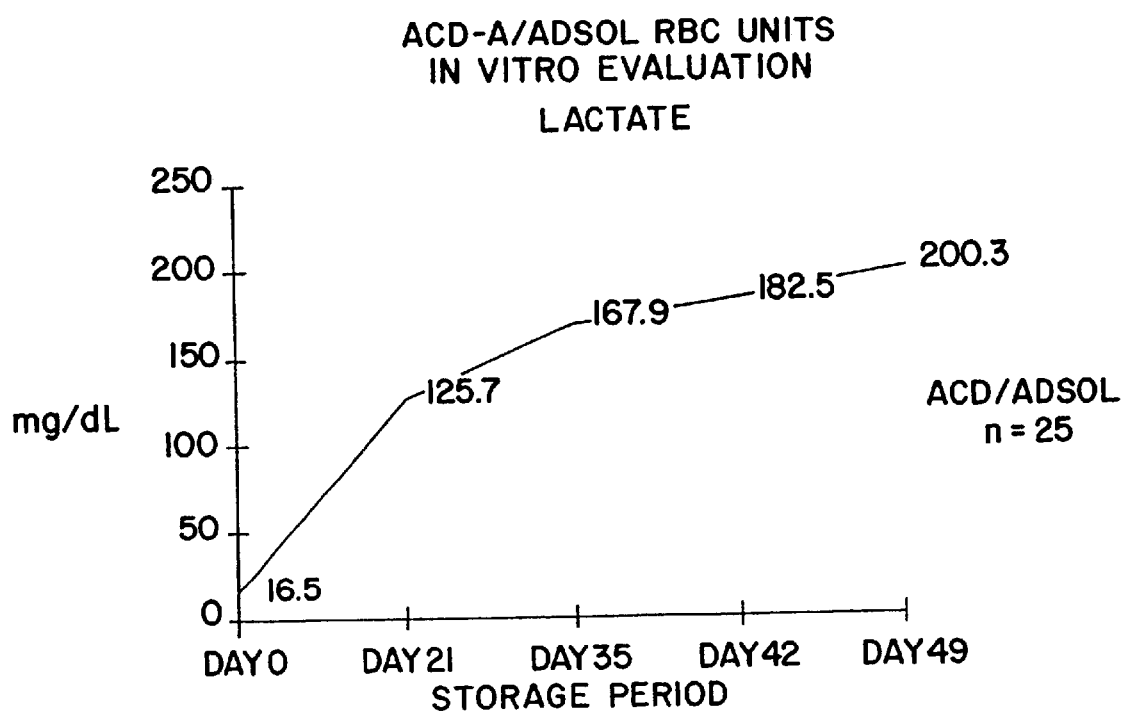
FIG. 21 is a graph showing the level of lactate in stored red blood cell compositions prepared in accordance with the present invention.
Figure 22:
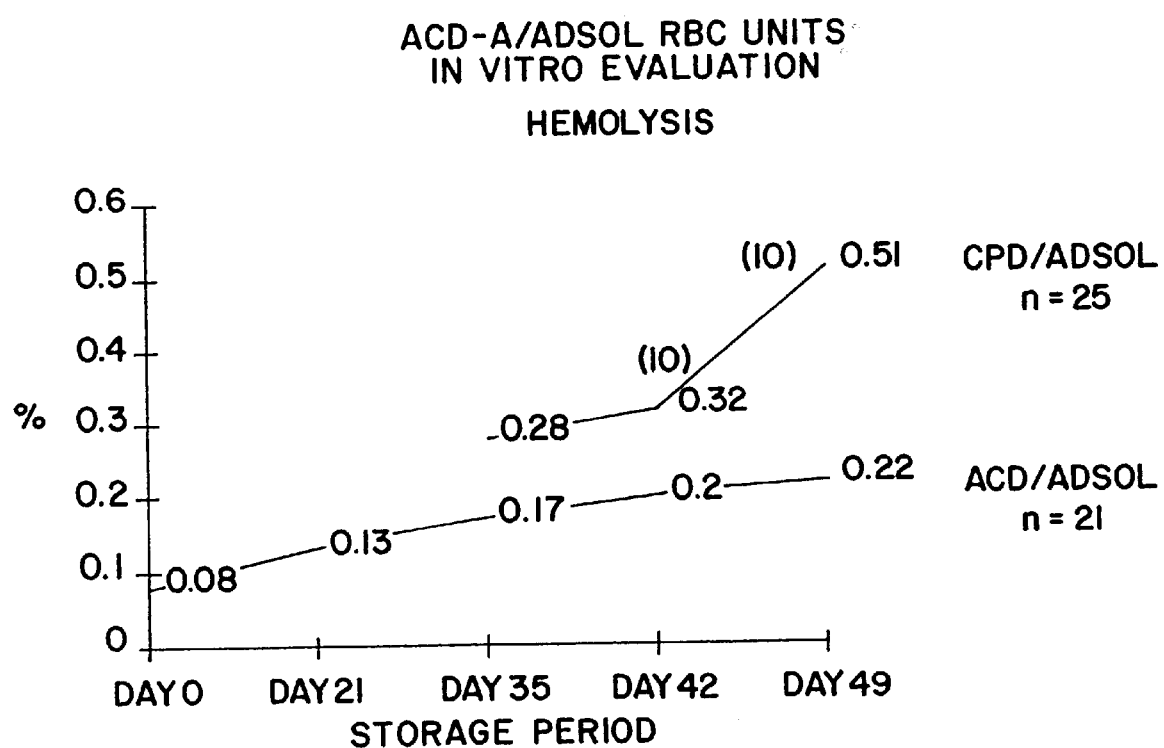
FIG. 22 is a graph comparing the levels of hemolysis in stored red blood cell compositions prepared in accordance with the present invention and red blood cell compositions prepared by a different method.

FIG. 14 shows in graphical form the relationship discovered between HCT$_{WB}$ and RATE$_{WB}$ for a rotating membrane separation device 52 of the type described above. FIG. 14 demonstrates the general principle that, as HCT$_{WB}$ increases, RATE$_{WB}$ must be increased to optimize EFF sufficient to obtain a consistent, uniform high $HCT_{RBC}$. This is because (see Equation (1)), as $RATE_{WB}$ decreases, EFF is increased, as long as other operating conditions remain the same.

It is necessary to consider both the relationship between $HCT_{WB}$ and $RATE_{WB}$ and the relationship between $HCT_{WB}$ and ROTOR at the same time. This is because, as $HCT_{WB}$ decreases, it is not always possible to increase ROTOR high enough to alone optimize EFF because of the constraints imposed by $ROTOR_{MAX}$ and $AHCT_{MAX\ or\ MIN}$.

The relationship expressed in the graph in FIG. 14 can be expressed mathematically and solved for $RATE_{WB}$, as follows:

$$RATE_{WB} = \left[ \frac{RATE_{MAX} - RATE_{MIN}}{AHCT_{MAX} - AHCT_{MIN}} \times (AHCT_{WB} - AHCT_{MIN}) \right] + RATE_{MIN} \quad (7)$$

where:
$RATE_{MAX}$ and $RATE_{MIN}$ are, respectively, the maximum and minimum flow rates (expressed in ml/min) set for the pump 20, taking into account $AHCT_{MAX}$ and $AHCT_{MIN}$. These flow rates are established by the manufacturer taking into account operational constraints of the pump 20 and clinical or experimental experience. $RATE_{MIN}$ takes into account, given the prescribed range of minimum and maximum hematocrits, minimum flow rate conditions required for effective separation conditions in the separation device 52 without unduly prolonging exposure to the blood to the high shear conditions present within the gap 60, thereby causing trauma. $RATE_{MAX}$ takes into account, also given the prescribed range of minimum and maximum hematocrits, maximum flow rates of drawing whole blood from a typical donor without causing discomfort or experiencing vein collapse. For the separation device 52 described above, and given the range of minimum and maximum hematocrits of 38% to 56%, nominal values of $RATE_{MAX}=100$ ml/min and $RATE_{MIN}=80$ ml/min can be used.

According to the invention, the controller 48 includes a separation enhancement element 146 (see FIG. 12) that augments the operation of the TMP control element 136 and the vein control element 144, by taking into account the interrelationships described above among $HCT_{WB}$, ROTOR, and $RATE_{WB}$.

The separation enhancement element 146 includes an input 148 that receives from the operator the value of $HCT_{WB}$ for the individual donor whose blood is to be collected. The input 148 also receives from the donor the selected anticoagulant ratio AC. From these, the separation enhancement element 146 calculates $AHCT_{WB}$, using Equation (5). The input 148 receives also receives the targeted red blood cell collection volume ($RBC_{Target}$) and the targeted plasma collection volume ($PLASMA_{Target}$) from the operator at the outset of a given procedure. The input 148 can comprise touch pad entry keys 150 on the device 12 (as FIG. 1 shows).

The separation enhancement element 146 includes in manufacturer-installed memory the prevailing set operating parameters $RATE_{MAX\ and\ MIN}$; $ROTOR_{MAX\ and\ MIN}$; and $AHCT_{MAX\ and\ MIN}$.

From this input, the separation enhancement element 146 derives ROTOR according to the relationships expressed in Equation (6). The separation enhancement element 146 also derives from this input $RATE_{WB}$ according to the relationships expressed in Equation (7).

The separation enhancement element 146 commands the TMP control element 136 to derived $TMP_{SET}$ using the enhanced fluid characteristic curve 138(1) that the particular combination of $HCT_{WB}$; ROTOR; and $RATE_{WB}$ defines.

The separation enhancement element 146 also commands the driver 46 to spin the rotor 58 at ROTOR. The construct of Equation (6) assures that $ROTOR_{MIN} \leq ROTOR \leq ROTOR_{MAX}$.

The separation enhancement element also commands the vein control element 144 to maintain pump 20 at $RATE_{WB}$. The construct of Equation (7) assures that $RATE_{MIN} \leq RATE_{WB} \leq RATE_{MAX}$.

The vein control element 144 controls the pump 20 at $RATE_{WB}$, unless sensed $P1 \leq P_{SET}$, indicating a vein collapse condition. In this instance, the vein control element 144 reduces $RATE_{WB}$ by a prescribed percentage increment (for example, by 5% of $RATE_{WB}$). The vein control element 144 also commands the driver 46 to reduce ROTOR based upon functions of Equations (6) and Equation (7), as the family of curves shown in FIG. 15 demonstrate.

Figure 15:
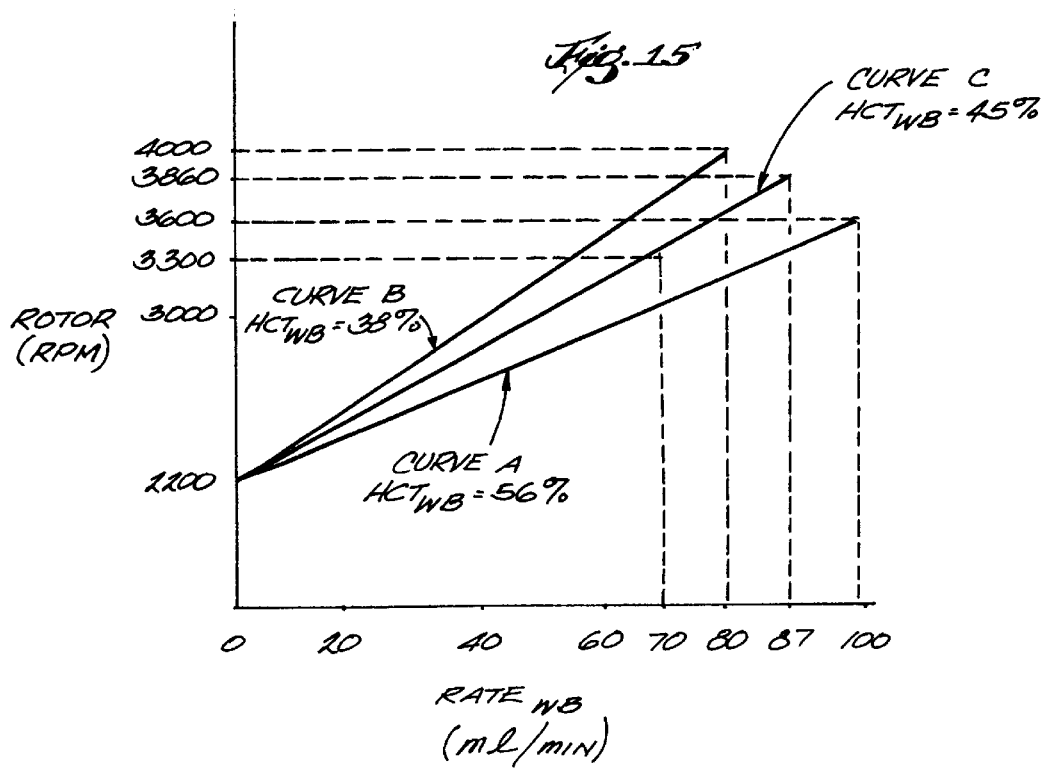
FIG. 15 shows a family of curves showing the relationship between donor hematocrit, the speed of rotation of the rotary membrane separation device, and the flow rate of whole blood, which is used by the vein control element to control the speed of rotation when a collapsed vein condition is detected, requiring a reduction of the flow rate of whole blood.

The x-axis of FIG. 15 shows $RATE_{WB}$ (in ml/min) increasing from the lowest possible flow rate ($RATE_{WB}=0$) to the maximum possible blood flow rate $RATE_{WB}$ prescribed according to the function expressed by Equation (7), given a $HCT_{WB}$ falling within the prescribed range of minimum and maximum hematocrits of 38% to 56%, and given the prescribed $RATE_{MAX}$ and $RATE_{MIN}$.

The y-axis of FIG. 15 shows ROTOR increasing from a prescribed minimum possible rotational rate permitted at $RATE_{WB}=0$ (which, for the device 54 described above, is set at 2200 RPM) to the maximum possible rotation rate ROTOR prescribed according to the function expressed in Equation (6), given a $HCT_{WB}$ again falling within the prescribed range of minimum and maximum hematocrits of 38% to 56%, and given the prescribed $ROTOR_{MAX}$ and $ROTOR_{MIN}$.

From this, a family of curves setting $RATE_{WB}$ as a function of ROTOR for a given $HCT_{WB}$ and can be drawn, three of which (Curves A, B, and C) are shown in FIG. 15. Curve A represents the $RATE_{WB}$/ROTOR function for maximum $HCT_{WB}=56\%$, extending from the intersection of $RATE_{WB}=0$/ROTOR=2200 to the intersection of $RATE_{WB}=100$ ml/min (derived by Equation (7))/ROTOR=3600 RPM (derived by Equation (6). Curve B represents the $RATE_{WB}$/ROTOR function for minimum $HCT_{WB}=38\%$, extending from the intersection of $RATE_{WB}=0$/ROTOR=2200 to the intersection of $RATE_{WB}=80$ ml/min (derived by Equation (7))/ROTOR=4000 RPM (derived by Equation (6). Curve C represents the $RATE_{WB}$/ROTOR function for an intermediate (and typical) hematocrit value $HCT_{WB}=45\%$, extending from the intersection of $RATE_{WB}=0$/ROTOR =2200 to the intersection of $RATE_{WB}=87$ ml/min (derived by Equation (7))/ROTOR =3860 RPM (derived by Equation (6).

Based upon the FIG. 15 family of curves, and given $HCT_{WB}$ and the incrementally reduced $RATE_{WB}$, the vein control element 144 derives ROTOR. For example, if $HCT_{WB}=45\%$, and the incrementally reduced $RATE_{WB}=70$ ml/min, ROTOR=3300 RPM.

If sensed P1 continues to indicate a vein collapse condition, the vein control element 144 makes another incremental decrease to the pump rate and adjustment to the rate of rotation, as above described, and so on until the collapsed vein condition is eliminated. The vein control element 144 then proceeds to incrementally increase the pump rate and adjust the speed of rotation over time, as above described, to seek to return the pump rate to $RATE_{WB}$ and the rotor driver rate to ROTOR, or as close to these prescribed conditions that P1 will allow.

The vein control element 144 also controls the pump 18 in synchrony with the pump 20 to assure that the desired anticoagulant ratio AC is maintained.

Meanwhile, the TMP control element 136 senses P2 and commands the pump 22 at a RATE$_{RBC}$ that will maintain P2=TMP$_{SET}$.

Concurrent with the operation of the TMP control element 136 and vein control element 144 as just described, the separation enhancement element 146 receives input from the weight scales 38 and 40, relating to the volumes of concentrated red blood cells and plasma being collected. The element 146 commands a toggle control element 152 based upon this input, the RBC$_{Target}$, and the PLASMA$_{Target}$ specified by the operator. The element 152 toggles the system 10 between operation in successive blood draw modes and blood return modes, consistent with conventional single needle procedures.

During the blood draw mode, the system 10 operates the pump 20 in the forward direction to draw whole blood from the donor for separation into red blood cells, which collect in the container 102, and plasma, which collects in the container 98. After a first prescribed volume of concentrated red blood cells is processed, the separation enhancement element 146 commands the element 152 to switch the system 10 to a return mode. During the return mode, the system 10 operates the pump 20 in the reverse direction to draw concentrated red blood cells from the container 102 for return to the donor. The separation enhancement element 146 compares collected plasma and red blood cell volumes to RBC$_{Target}$ and PLASMA$_{Target}$ and derives a second prescribed volume of whole blood to be processed. The separation enhancement element 146 then commands the element 152 to switch the system 10 back to a draw mode to collect this prescribed volume. The separation enhancement element 146 continues to command toggling between successive draw and return modes, while monitoring the weight scales 38 and 40, until RBC$_{Target}$ and PLASMA$_{Target}$ are achieved.

In the illustrated and preferred embodiment, while red blood cells collect in the container 102, the separation enhancement element 146 also samples the output of the weight scale 38 over time. The separation enhancement element 146 derives the actual flow rate RATE$_{RBC-Real}$ of red blood cells into the container by the change in container 102 weight over time. The separation enhancement element 146 compares RATE$_{RBC-REAL}$ to RATE$_{RBC}$ commanded by the TMP control element 136 and derives a difference, if any. The separation enhancement element 146 periodically issues adjustment commands to the pump 22 based upon the difference to assure that RATE$_{RBC-Real}$ corresponds to the command RATE$_{RBC}$ issued by the TMP control element 136.

Likewise, in the illustrated and preferred embodiment, while plasma collects in the container 98, the separation enhancement element 146 samples the output of weight scale 40 over time. The separation enhancement element 146 derives the actual flow rates of plasma RATE$_{PLASMA-Real}$ of plasma into the container 98 by the change in container 98 weight over time. The separation enhancement element 146 adds RATE$_{PLASMA-Real}$ and RATE$_{RBC-REAL}$ to derive RATE$_{WB-Real}$. Alternatively, the separation enhancement element 146 can convert RATE$_{RBC-Real}$ into RATE$_{WB-Real}$, without using the weight scale 40 output to derive RATE$_{PLASMA-Real}$, as follows:

$$RATE_{WB-Real} = RATE_{RBC-Real} + \frac{(1 - HCT_{WB})}{HCT_{WB}} RATE_{RBC-Real} \quad (8)$$

The separation enhancement element 146 compares the derived RATE$_{WB-Real}$ to RATE$_{WB}$ commanded by the vein control element 144 (as above described) and derives a difference, if any. The separation enhancement element 146 periodically issues adjustment commands to the pump 20 based upon the difference to assure that RATE$_{WB-Real}$ corresponds with the command RATE$_{WB}$ issued by the vein control element 136.

EXAMPLE 1

FIGS. 4 to 9 and Table 2 exemplify the operation of the system shown in FIGS. 1 to 3 under the control of the controller 48 in a manner that embodies the features of the invention.

In this Example, a rotating membrane separation device of the type and dimensions describe above is used. In this Example, the operator enters the following prescribed condition inputs to the separation enhancement element 146:

HCT$_{WB}$=46(%)
RBC$_{Target}$=250 ml
PLASMA$_{Target}$=475 ml
RATE$_{MAX}$=100 ml/min
RATE$_{MIN}$=80 ml/min
ROTOR$_{MAX}$=4000 RPM
ROTOR$_{MIN}$=3600 RPM
AHCT$_{MAX}$=56(%)
AHCT$_{MIN}$=38(%)
AC=8(%)

Based upon this input, the separation enhancement element 146 derives

ROTOR=3835 RPM
RATE$_{WB}$=88 ml/min

At the beginning of the procedure, the TMP control element 136 derives TMP$_{SET}$ and the vein control element 144 sets P$_{SET}$.

The separation enhancement element 146 commands three successive draw/return cycles. The following Table 2 summarizes the blood volumes and times for the three cycles.

TABLE 2

| CYCLE | WHOLE BLOOD VOLUME (ML) | RED BLOOD CELL VOLUME (ML) | PLASMA VOLUME (ML) | SALINE VOLUME (ML) | TIME (MIN) |
|---|---|---|---|---|---|
| 1. DRAW | 451 | 275 | 148 | | 5.26 Note: 28 ml constitutes residual priming volume |
| RETURN | 0 | −275 | 0 | 0 | 2.11 |
| 2. DRAW | 473 | 275 | 198 | 0 | 5.26 |
| RETURN (SALINE) | 0 | 0 | 0 | 240 | 1.85 |
| RETURN (RED BLOOD CELLS) | 0 | −179 | 0 | 0 | 1.38 |

TABLE 2-continued

| CYCLE | WHOLE BLOOD VOLUME (ML) | RED BLOOD CELL VOLUME (ML) | PLASMA VOLUME (ML) | SALINE VOLUME (ML) | TIME (MIN) |
|---|---|---|---|---|---|
| 3. DRAW | 308 | 179 | 129 | 0 | 3.42 |
| RETURN | 0 | −25 | 0 | 0 | .19 |
| TOTALS | 1232 | 250 | 475 | 240 | 19.47 |

Figure 4:
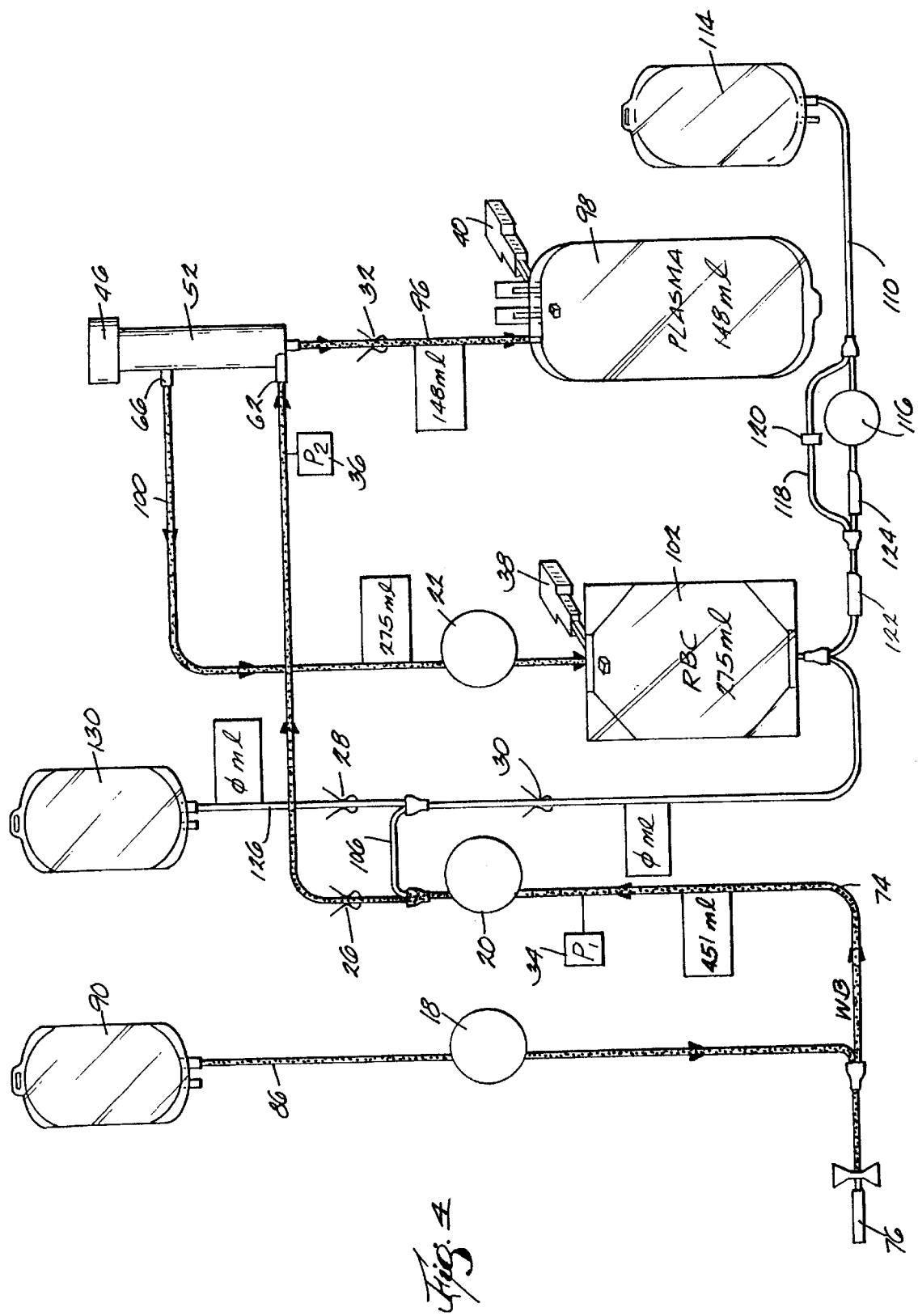
FIG. 4 is a schematic view of the blood collection system shown in FIG. 1 being operated in a first draw cycle.
Figure 5:
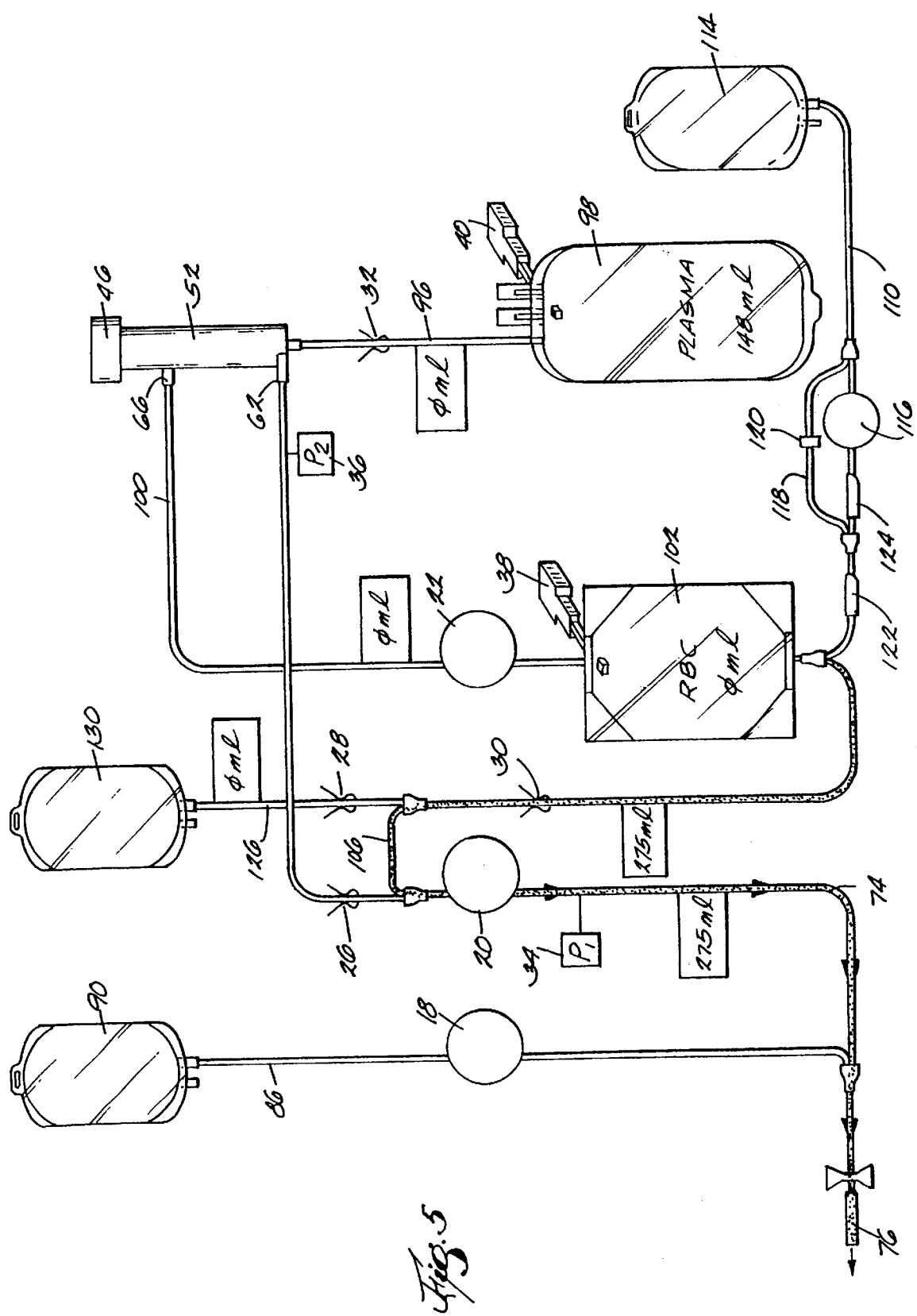
FIG. 5 is a schematic view of the blood collection system shown in FIG. 1 being operated in a first return cycle.

FIG. 4 schematically shows fluid flow and associated fluid volumes using the Cycle 1 draw mode. FIG. 5 schematically shows fluid flow and associated fluid flow volumes during the Cycle 1 return mode.

Figure 6:
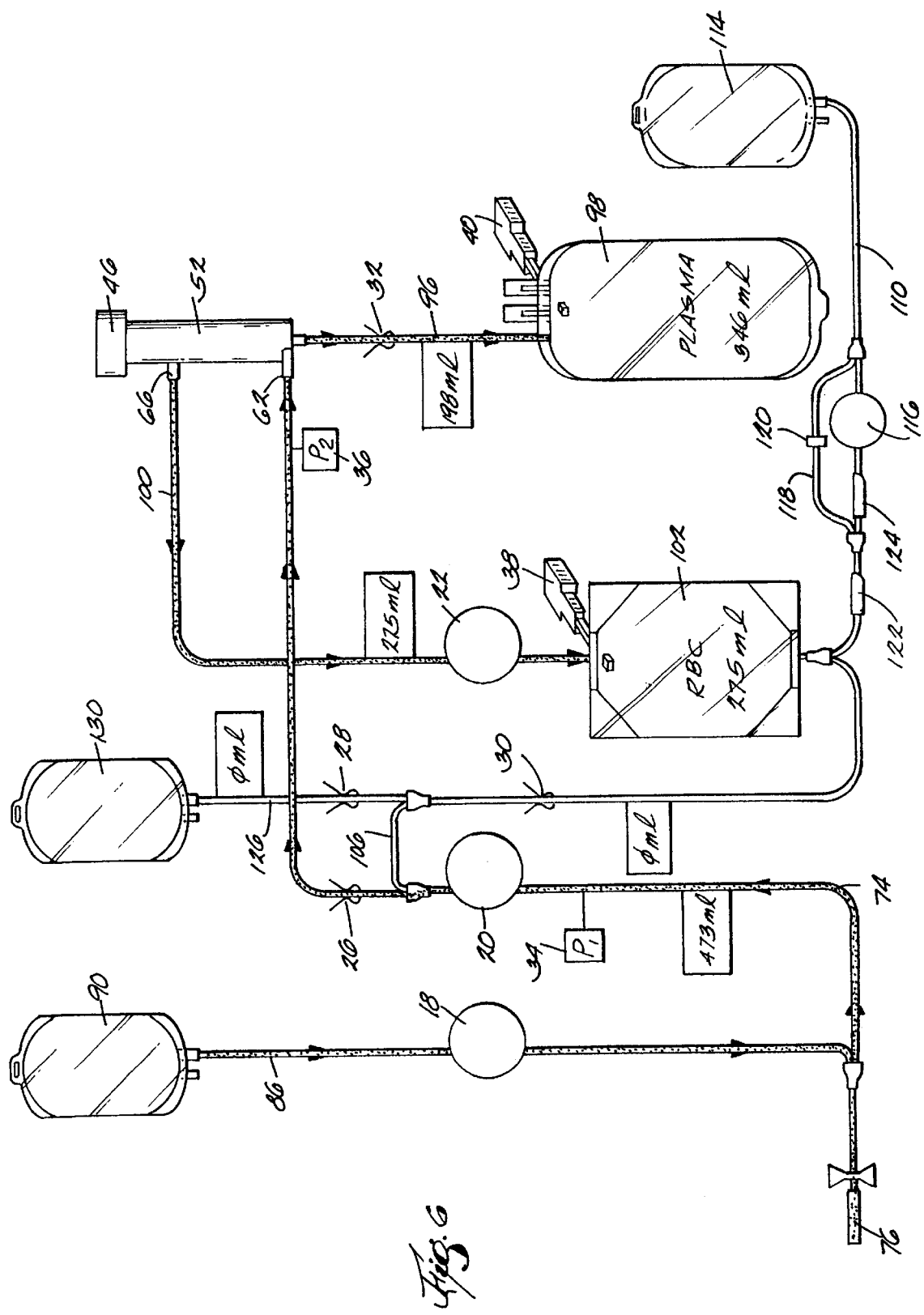
FIG. 6 is a schematic view of the blood collection system shown in FIG. 1 being operated in a second draw cycle.
Figure 7:
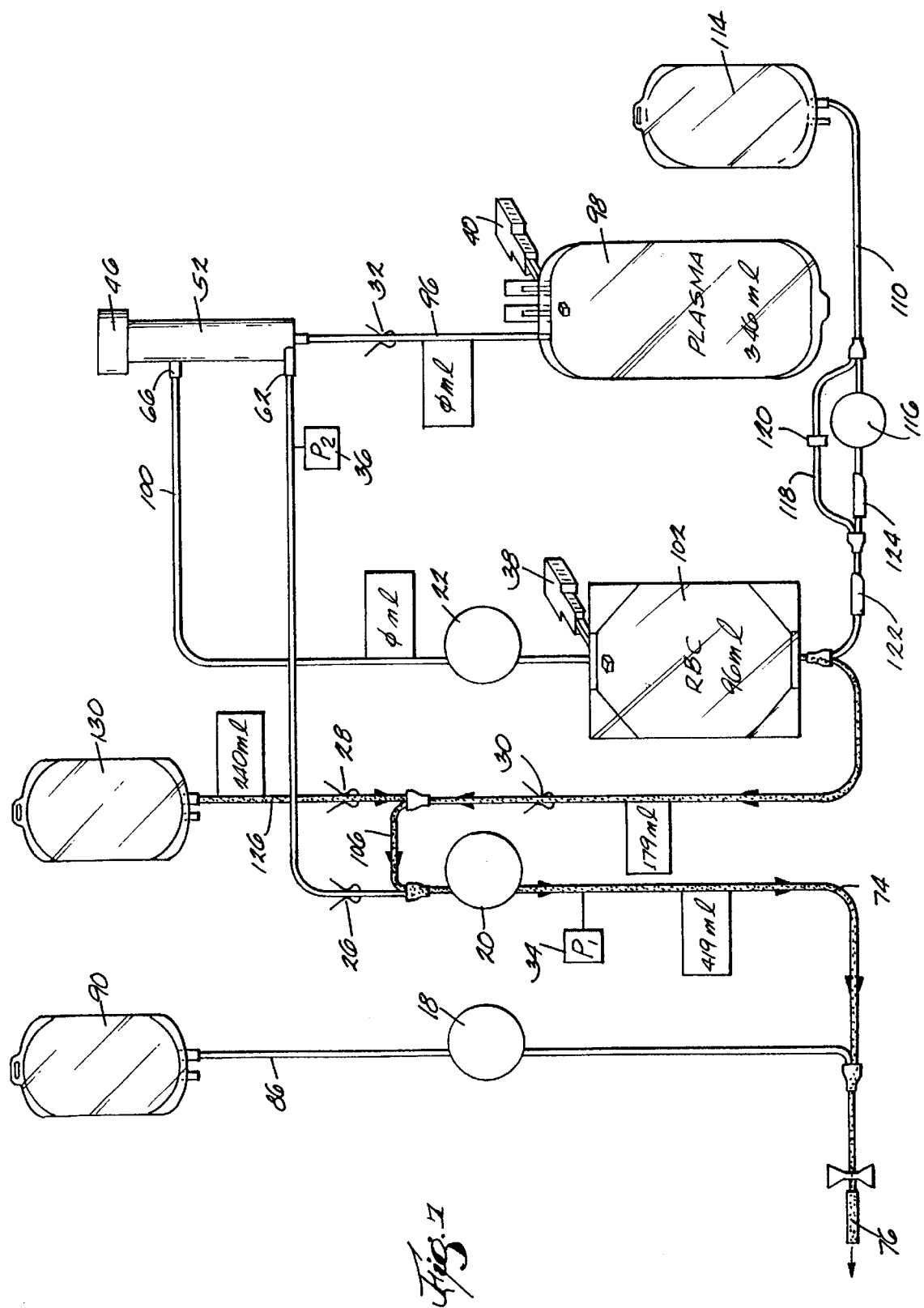
FIG. 7 is a schematic view of the blood collection system shown in FIG. 1 being operated in a second return cycle.

FIG. 6 schematically shows fluid flow and associated fluid flow volumes during the Cycle 2 draw mode. FIG. 7 schematically shows fluid flow and associated fluid flow volumes during the Cycle 2 return mode, during which red blood cells and saline are sequentially returned to the donor, with saline being returned first, followed by red blood cells.

Figure 8:
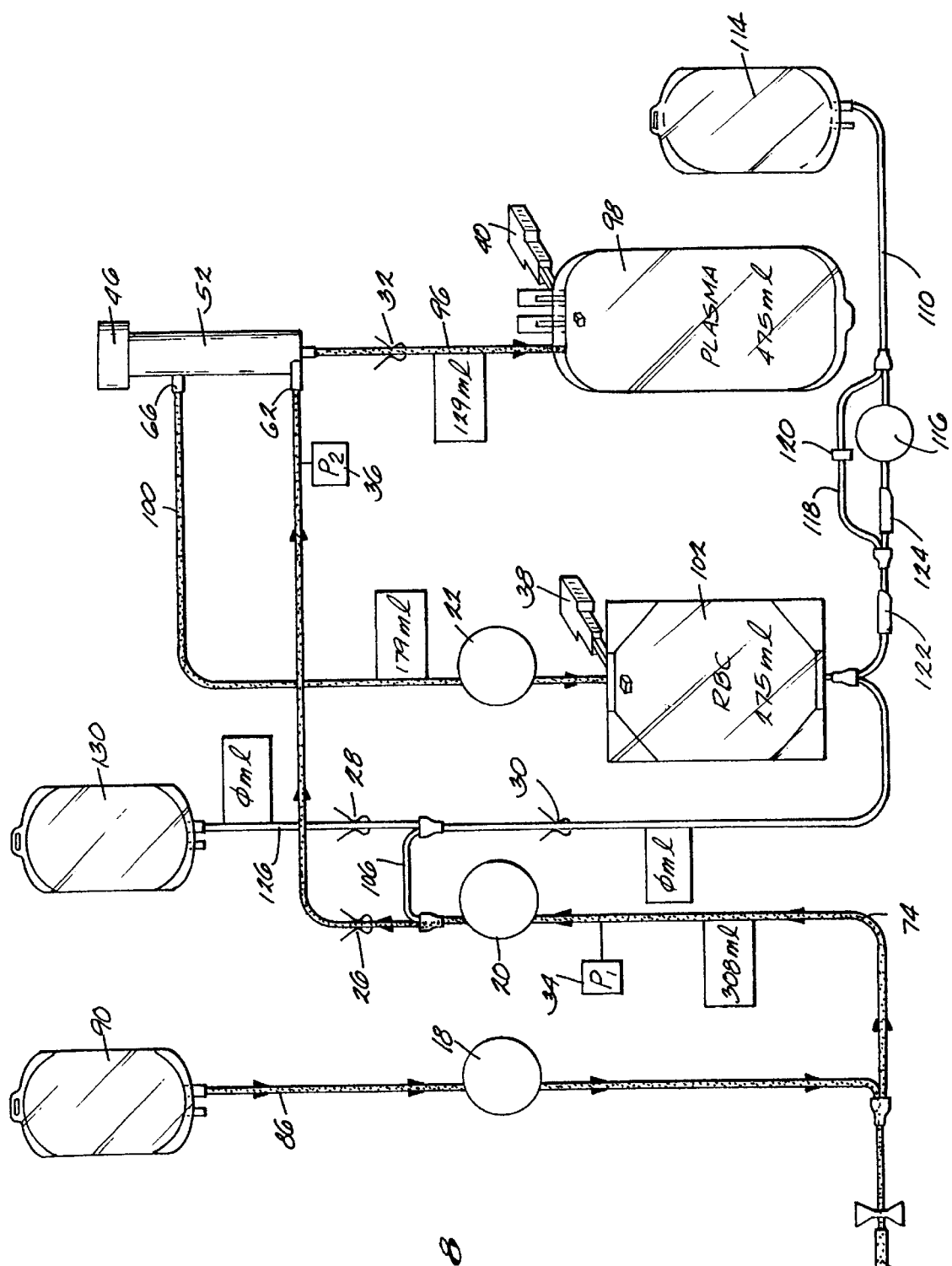
FIG. 8 is a schematic view of the blood collection system shown in FIG. 1 being operated in a third and final draw cycle.
Figure 9:
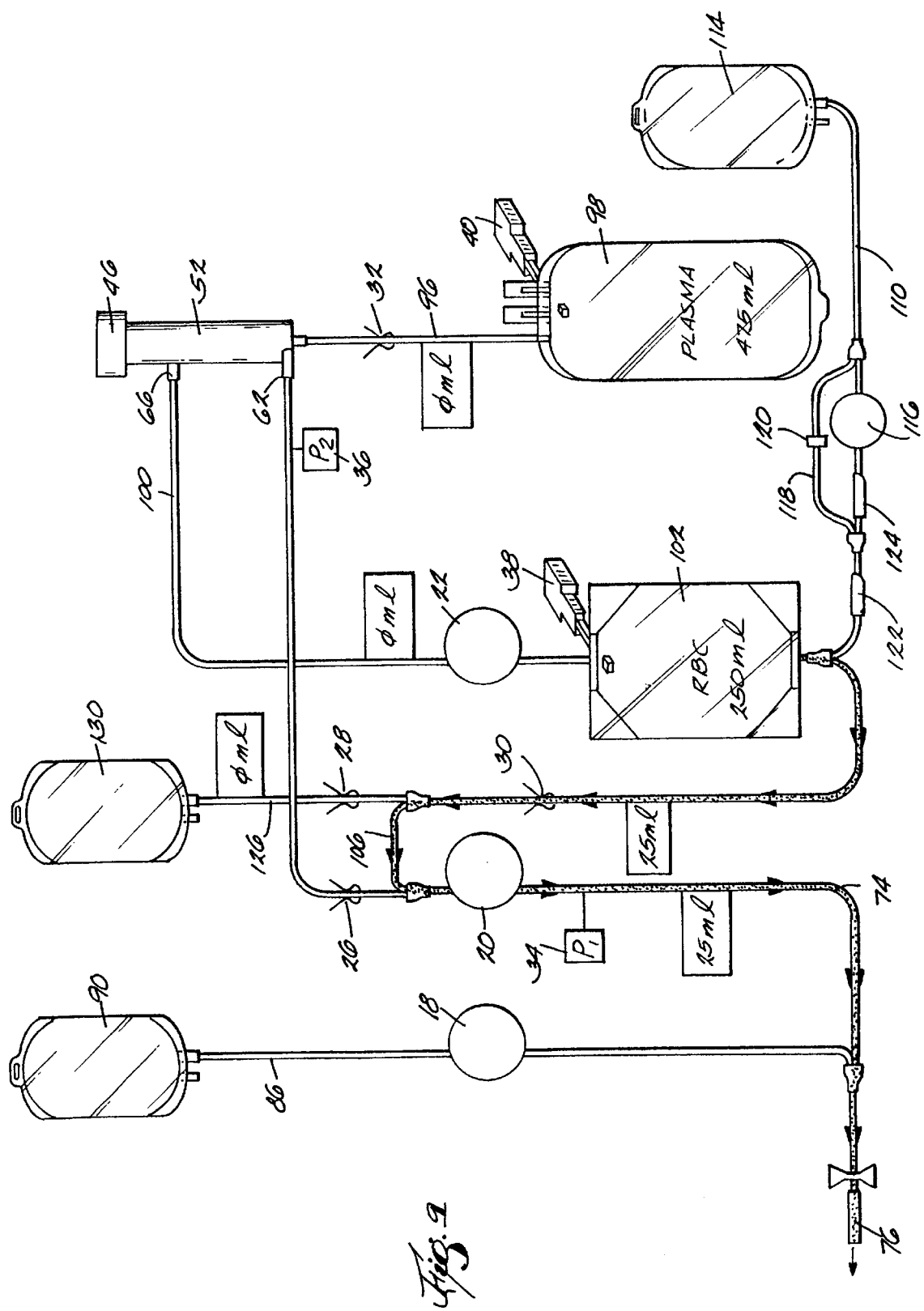
FIG. 9 is a schematic view of the blood collection system shown in FIG. 1 being operated in a third and final return cycle.

FIG. 8 schematically shows fluid flow and associated fluid flow volumes during the Cycle 3 draw mode. FIG. 9 schematically shows fluid flow and associated fluid flow volumes during the Cycle 3 final return mode.

D. Leukoreduction of Collected Red Blood Cells

Figure 10A:
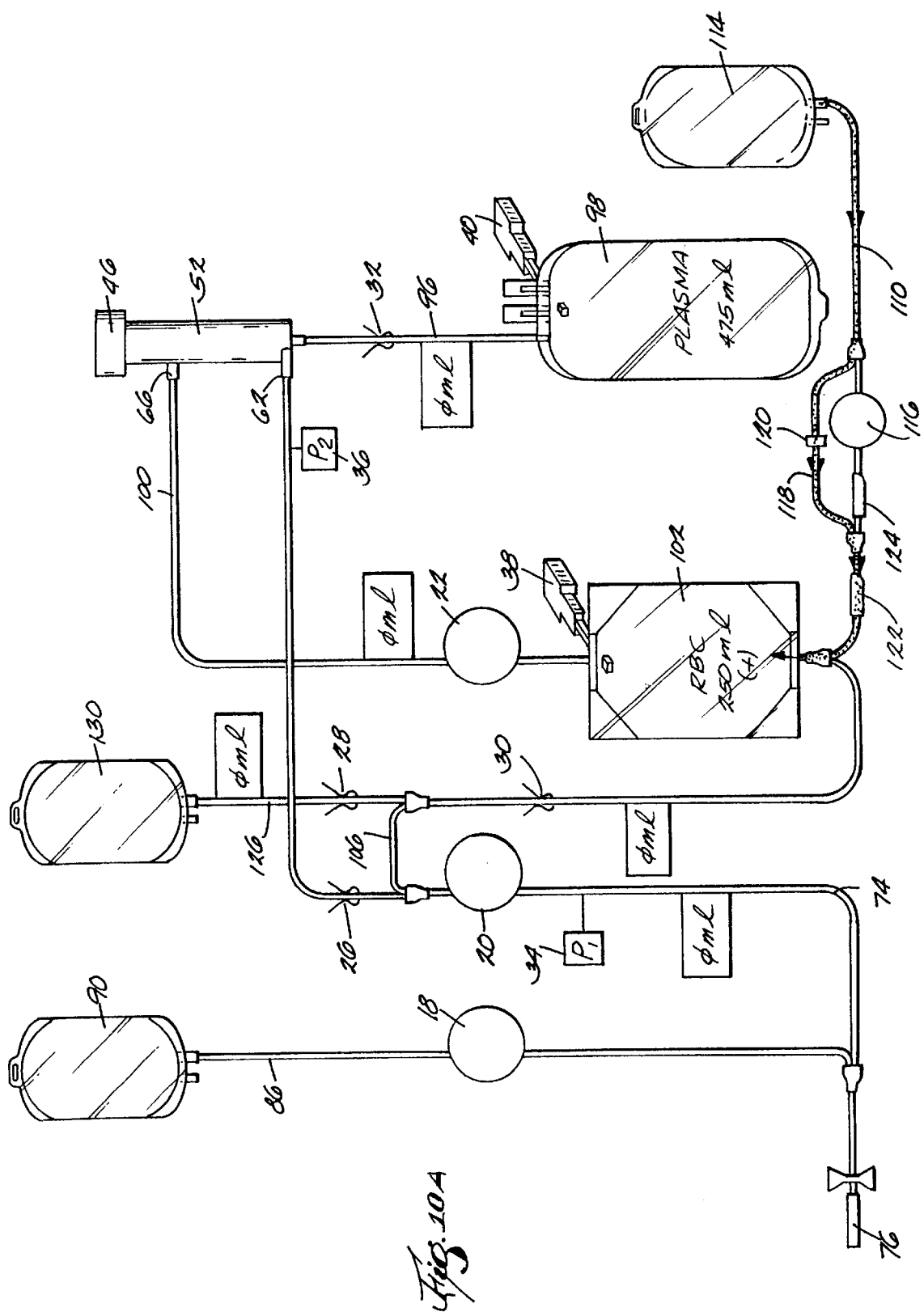
FIGS. 10A and B are schematic views of the blood collection system shown in FIG. 1 being manipulated to remove leukocytes from the concentrated red blood cells before storage.

In the illustrated and preferred embodiment (see FIG. 2), the set 14 includes a leukoreduction filter 116, as previously described. FIGS. 10A and B show the sequence of using the filter 116 to remove leukocytes from the concentrated red blood cells collecting the preceding Example. The sequence is performed manually, after the donor has been disconnected from the system 10.

The operator first opens the roller clamp 122. The operator takes the container 114 off the support 44 and lifts it above the container 102. The operator transfers by gravity flow the storage solution from the container 114 (as FIG. 10A shows), through the bypass path 118 with the one-way valve 120 and the sixth and fifth tubes 110/104 into the red blood cells in the container 102 (which is still preferably supported on the weight scale 38 at this time). The operator preferably returns the container 114 (now empty) to the support 44. The container 102 now contains the volume of collected red blood cells and the additional volume of storage solution (indicated as 250 ml(+) in FIG. 10A).

Figure 10B:
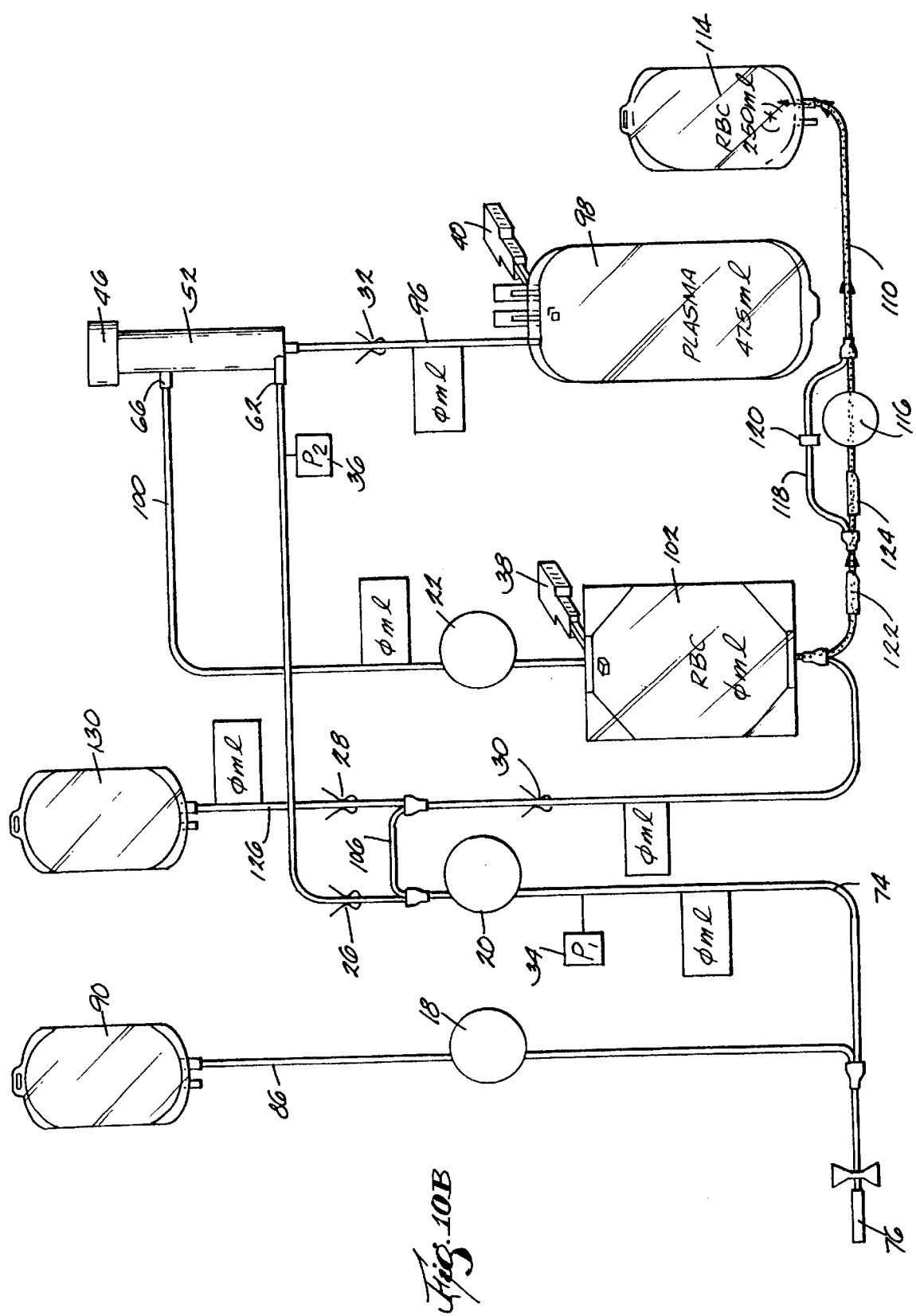

The operator takes the container 102 off the weight scale 38 and gently squeezes the container 102 to mix the red blood cells with the storage solution in the container 102. The operator then opens the roller clamp 124 and lifts the container 102 above the container 114 (now on the support 44). Red blood cells and storage solution flow through the fifth tube 104, sixth tube 110, and through the filter 116 into the container 114 (as FIG. 10B shows). Leukocytes are thereby removed from the red blood cells.

The leukocyte-reduced red blood cells and resident storage solution are retained in the container 114 for long term storage. The container 114 holds the collected volume of red blood cells plus the additional volume of storage solution (designated 250 ml(+) in FIG. 10B). The collected volume of plasma is likewise retained in the container 98 for storage or further processing. The containers 114 and 98, along with the other containers and tubing associated with the set 14, are made from conventional approved medical grade plastic materials, such as polyvinyl chloride plasticized with di-2-ethylhexyl-phthalate (DEHP). Containers made from such materials are known to demonstrate characteristics beneficial to the storage of red blood cells.

The containers 114 and 98, with the blood components they hold, are separated from the set 14 by forming snap-apart seals in the tubes 104, 100, and 110, using, for example, a conventional heat sealing device like the Hematron® dielectric sealer sold by Baxter Healthcare Corporation.

The inventors have further discovered that red blood cells processed in the rotating membrane separating device 52 and collected according to the invention in high hematocrit concentrations, demonstrate significantly lower hemolysis levels before and after long term storage in a leukocyte-reduced condition, compared to comparable high hematocrit concentrations collected according to the invention in which the population of leukocytes is not reduced. The following Table 3 summarizes the difference of hemoglobin levels under such conditions using commercially available leukocyte filters (Filter 1=PALL™ WBF1 and Filter 2=Asahi SEPACELL™ RS2000).

TABLE 3

|  | Collected Using System 10 With Pre-Storage Leuko-reduction (Filter 1)* | Collected Using System 10 with Pre-Storage Leuko-reduction (Filter 2)* | Collected Using System 10 Without Pre-Storage Leuko-Reduction | Manually Collected Unfiltered Red Blood Cells |
|---|---|---|---|---|
| Avg $HCT_{RBC}$ | 68.7% | 69.4% | Comparable to foregoing columns | Typically about 70% |
| Measured Hemolysis (%) Storage Day 0** (10 Samples) | 0.08% ± 0.02 | 0.06% ± 0.01 | about 0.13% | Typically about 0.08% |
| Measured Hemolysis (%) Storage Day 42** (Same 10 Samples) | 0.30% ± 0.04 | 0.36% ± 0.17 | about 0.82% | Typically about 0.56% |

*Note: Both Filter 1 and Filter 2 reduced leukocyte (white blood cell) levels below $1 \times 10^5$.
**Note: The red blood cell concentrations were stored in association with ADSOL ® Storage Media, sold by Baxter Healthcare Corporation.

Table 3 shows acceptable hemolysis levels exist in high concentrated red blood cell products collected according to the invention (columns 1 to 3). Table 3 also demonstrates that reducing the number of leukocytes from the highly concentrated red blood cell products reduces the hemolysis levels both at the outset of storage and at the end of the storage period (columns 1 and 2), compared to highly concentrated red blood cells products that were not leuko-reduced before storage (column 3).

As set forth above, one aspect, the present invention is directed to a method for providing viable red blood cells. The method may include but is not limited to, using a separation device of the type generally described above. In accordance with the method, whole blood obtained from a donor is combined with anticoagulant. Several different anticoagulant formulations are known and may be used to collect red cells in accordance with the present invention. For example, the anticoagulant most commonly used for collection of red cells is citrate-phosphate-dextrose (CPD) which includes trisodium citrate, citric acid, monobasic sodium phosphate and dextrose. Other available anticoagulants include the acid citrate dextrose (ACD) solutions A and B. In the preferred embodiment, whole blood is combined with ACD, Solution A (ACD-A). One (1) liter of ACD-A includes 22.0 g of trisodium citrate, 7.3 g citric acid, 24.50 g of dextrose and 1 l of water. Unlike CPD, ACD-A does not include phosphate.

The amount of anticoagulant combined with blood must be sufficient to prevent the clumping of blood cells or coagulation of plasma of the blood cells during processing. On the other hand, too much anticoagulant may result in excess citrate being reinfused to the donor or infused to the recipient, resulting in a "citrate reaction," the symptoms of which may include anxiety, chills, and tingling sensations around the mouth and fingers. Accordingly, the ratio of whole blood to anticoagulant should be between approximately 8:1 and 14:1 with a preferred ratio of approximately 12:1 (i.e. 8% ACD/Whole Blood).

The collected and concentrated red cells, which may include plasma and some residual anticoagulant, are combined with a quantity of a storage solution which allows for extended storage of the red cell concentrate. Storage solutions for red cells are known. Storage solutions which may be useful in the method of the present invention are described, for example, in U.S. Pat. No. 5,248,506. One such storage solution which is preferred for storage of red cells collected in accordance with the present invention is a solution that includes adenine, mannitol, dextrose and sodium chloride. Such a solution is described in U.S. Pat. No. 4,267,269, which is incorporated by reference, and which is commercially available under the name Adsol® and sold by Baxter Healthcare Corporation of Deerfield, Ill. One liter of Adsol® includes approximately 22.0 g of dextrose, 0.27 g adenine, 7.5 g mannitol and 9.0 g of sodium chloride. Of course, it should be understood that other solutions which may contain some, but not all, of the components of Adsol® may also be used for storing red cell. In one embodiment of the present invention, a red cell composition having a total volume of approximately 250 ml (which includes plasma and anticoagulant) is combined with approximately 100 ml of Adsol®.

Collection of red cells in accordance with the above-described methods provides a viable red cell composition suitable for extended storage without compromising the viability of the red blood cells. As shown in FIGS. 16–22, the ATP, 2,3-DPG, potassium and pH levels were comparable to, if not better than, the levels obtained in manually collected red cells using CPD as the anticoagulant for the whole blood and stored in 100 ml of Adsol® solution. With respect to hemolysis, red blood cells collected in accordance with the method described above showed results superior to hemolysis levels of manually collected red cells (using CPD as the anticoagulant and Adsol® as the storage media) and superior to hemolysis levels in any other reported collections of red blood cells. A description of the procedure used to collect red cells in accordance with the above-described method is set forth below.

EXAMPLE

Twenty three (23) units of red blood cells were collected from donors using the separation device of the type generally described above. A total of approximately 1223 ml (±404 ml) was processed through a rotating membrane separation device of the type described above for approximately 25 minutes, (+8 min.) at a rotational speed of approximately 3800 rpm. The whole blood was anticoagulated with ACD-A solution in a ratio of approximately 12:1 whole blood to anticoagulant. Approximately 250 ml of red blood cells having a hematocrit of approximately 70% were collected and combined with approximately 100 ml of Adsol® solution added to the red blood cells immediately after collection. The red cells were leukoreduced at room temperature using a Pall WBF 1 or Asahi RS2000 leukoreduction filter and stored for 49 days at 4° C.±2° C. In vitro red blood cell function assays were performed at 0, 21, 35, 42 and 49 days of storage. The results from some of the units (where n=12) are reported in Table 1 below. The results from all of the units (where n=23) are reported in FIGS. 16–22.

TABLE 1

| Days | Hemolysis % | ATP (umol/mL) | ATP (% of init.) | 2,3-DPG (umol/mL) | K+ mEq/L |
|---|---|---|---|---|---|
| 0  | 0.09 (0.02) | 66 (7)  | 100 | 1.7 (0.2) | 1.9 (0.1) |
| 21 | 0.14 (0.03) | 65 (11) | 98  | *         | 22.2 (3.0) |
| 35 | 0.16 (0.04) | 60 (8)  | 91  | *         | 29.8 (2.2) |
| 42 | 0.19 (0.08) | 54 (7)  | 82  | *         | 33.2 (2.6) |
| 49 | 0.23 (0.09) | 45 (7)  | 69  | *         | 36.5 (2.8) |

*Below detection limit; standard deviations are shown in parentheses.

As shown in Table 1 and also in FIGS. 16–22, collection of red blood cells using ACD-A as the anticoagulant for whole blood and Adsol® as the storage media resulted in a viable red cell product.

Also, as set forth in Table 1 (n=12) and FIG. 10 (n=23), the percent hemolysis levels at day 42 and day 49 were well below the 1.0% maximum acceptable value required by the Food and Drug Administration and also below the 0.8% level suggested for Europe. Levels of ATP were also well preserved throughout the storage. On the basis of the above, whole blood collected using ACD as the anticoagulant and Adsol® solution can be used to store the red blood cells collected by automated blood collection for at least 49 days.

The red cell compositions obtained in accordance with the above-described method (wherein final hematocrit of the collected red cells is approximately 70%) may include between 160–240 ml of red blood cells, 20–100 ml of plasma, 5–15 ml of anticoagulant and 80–120 ml of the storage solution. More specifically, the red cell composition may include approximately 175–185 ml of red blood cells, 60–70 ml of plasma, 6–10 ml of anticoagulant and 90–110 ml of storage solution. Stated as a percentage of the total volume of the red cell composition, (which includes red cell concentrate, anticoagulant, plasma and storage solution), the red cell composition may include between about 40–79% red cell concentrate, between about 1–5% anticoagulant, 5–30% of the plasma and 20–40% storage solution. Of course, these volumes and/or percentages will vary depending on the donor hematocrit and donor weight.

While the invention has been described in connection with the foregoing, specific embodiments, it is to be understood that the invention is not limited thereto. The present invention is intended to cover various modifications within the spirit and the scope of the appended claims.

That which is claimed:

1. A method for providing viable red blood cells comprising:
   a) providing a quantity of whole blood;
   b) combining said whole blood with a selected quantity of a phosphate-free anticoagulant, wherein one liter of said anitcoagulant comprises approximately 7.3 g of citric acid, 22.0 g of trisodium citrate and 24.5 g of dextrose;
   c) separating said anticoagulated whole blood into components to provide concentrated red blood cells;
   d) combining said concentrated red blood cells with a solution, wherein one liter of said solution comprises approximately 22.0 g dextrose, 0.27 g adenine, 7.5 g mannitol and 9.0 g sodium chloride.

2. The method of claim 1 further comprising:

a) providing a separation device;

b) establishing fluid communication between a donor and said blood separation device;

c) removing whole blood from a donor to provide said quantity of whole blood;

d) introducing said anticoagulated whole blood into said separation device; and e) separating said anticoagulated whole blood into components wherein one of the components comprises concentrated red blood cells while maintaining fluid communication between said donor and said blood separation device.

3. The method of claim 1 further comprising collecting at least a portion of said concentrated red blood cells in a container.

4. The method of claim 2 wherein said separation device comprises a membrane filtration device.

5. The method of claim 1 comprising passing said red blood cells through a filter for removing white blood cells.

6. The method of claim 3 further comprising sensing changes in the weight of said container as said concentrated red blood cells are collected in said container.

7. The method of claim 2 comprising returning at least a portion of said concentrated red blood cells to said donor.

8. The method of claim 5 wherein said red blood cells are suitable for storage for up to 42 days and wherein after storage for 42 days, the percent hemolysis of said red blood cells is less than about 0.4%.

9. A method for providing viable red blood cells comprising:

a) providing a quantity of whole blood;

b) combining said whole blood with a selected quantity of a phosphate-free anticoagulant, wherein one liter of said anticoagulant comprises approximately 7.3 g of citric acid, 22.0 g of trisodium citrate and 24.5 g of dextrose;

c) separating said anticoagulated whole blood into components to provide concentrated red blood cells;

d) combining said red blood cells with a solution, wherein one liter of said solution comprises approximately 22.0 g dextrose, 0.27 g adenine, 7.5 g mannitol and 9.0 g sodium chloride, whereby said red blood cells, if stored for a period of 42 days, maintain a red blood cell ATP level that is not less than approximately 80% of the initial ATP level at the beginning of the storage period.

* * * * *